US006569382B1

(12) United States Patent
Edman et al.

(10) Patent No.: US 6,569,382 B1
(45) Date of Patent: May 27, 2003

(54) METHODS APPARATUS FOR THE ELECTRONIC, HOMOGENEOUS ASSEMBLY AND FABRICATION OF DEVICES

(75) Inventors: Carl F. Edman, San Diego, CA (US); Michael J. Heller, Encinitas, CA (US); Rachel Formosa, San Diego, CA (US); Christian Gurtner, La Jolla, CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 09/436,311

(22) Filed: Nov. 8, 1999

Related U.S. Application Data

(63) Continuation-in-part of application No. 08/760,933, filed on Dec. 6, 1996, which is a continuation-in-part of application No. 08/534,454, filed on Sep. 27, 1995, now Pat. No. 5,849,486, which is a continuation-in-part of application No. 08/304,657, filed on Sep. 9, 1994, now Pat. No. 5,632,957, which is a continuation-in-part of application No. 08/271,882, filed on Jul. 7, 1994, now Pat. No. 6,017,696, which is a continuation-in-part of application No. 08/146,504, filed on Nov. 1, 1993, now Pat. No. 5,605,662, application No. 09/436,311, which is a continuation-in-part of application No. 08/703,601, filed on Aug. 23, 1996, now Pat. No. 5,849,489, which is a continuation of application No. 08/232,233, filed on May 5, 1994, now Pat. No. 5,565,322, which is a continuation-in-part of application No. 07/790,262, filed on Nov. 7, 1991, now Pat. No. 5,532,129, application No. 09/436,311, which is a continuation-in-part of application No. 09/129,470, filed on Aug. 5, 1998, now Pat. No. 6,329,143, which is a continuation of application No. 08/906,569, filed on Aug. 5, 1997, now Pat. No. 5,835,404, which is a continuation of application No. 08/258,168, filed on Jun. 10, 1994, now Pat. No. 5,787,032, and a continuation of application No. 08/968,065, filed on Dec. 5, 1997, now Pat. No. 6,029,764, which is a continuation-in-part of application No. 08/855,058, filed on May 14, 1997, now Pat. No. 6,048,690.

(51) Int. Cl.[7] ............................ G01N 15/00; G01N 1/00; C12Q 1/68
(52) U.S. Cl. ............................ 422/68.1; 422/50; 435/6
(58) Field of Search ............................ 435/6; 422/50, 422/68.1

(56) References Cited

U.S. PATENT DOCUMENTS 3,950,738 A    4/1976    Hayashi et al. ............. 365/185

(List continued on next page.)

FOREIGN PATENT DOCUMENTS

EP    0228075    7/1987

(List continued on next page.)

OTHER PUBLICATIONS

Anand et al., "Pulsed Field Gel Electrophoresis" *Gel Electrophoresis Of Nucleic Acids–A Practical Approach,.* 2nd Ed., Eds. D.Rickwood & B.D.Hames (New York:IRL Press), 101–123 (1990).

(List continued on next page.)

*Primary Examiner*—Ardin H. Marschel
(74) *Attorney, Agent, or Firm*—O'Melveny & Myers LLP

(57) ABSTRACT

Methods and apparatus are provided for the fabrication of microscale, including micron, sub-micron, and nanoscale, devices. Electronic transport of movable component devices is utilized through a fluidic medium to effect transport to a desired target location on a substrate or motherboard. Forces include electrophoretic force, electroosmotic force, electrostatic force and/or dielectrophoretic force. In the preferred embodiment, free field electroosmotic forces are utilized either alone, or in conjunction with, other forces. These forces may be used singly or in combination, as well as in conjunction with yet other forces, such as fluidic forces, mechanical forces or thermal convective forces. Transport may be effected through the use of driving electrodes so as to transport the component device to yet other connection electrodes. In certain embodiments, the connection electrodes may also be utilized, either alone or in combination with driving electrodes, to electronically transport the component device to the connection electrodes.

12 Claims, 15 Drawing Sheets

U.S. PATENT DOCUMENTS

| | | | |
|---|---|---|---|
| 3,995,190 A | 11/1976 | Salgo | 313/391 |
| 4,032,901 A | 6/1977 | Levinthal | 365/118 |
| 4,563,419 A | 1/1986 | Ranki et al. | 435/6 |
| 4,580,895 A | 4/1986 | Patel | 356/39 |
| 4,584,075 A | 4/1986 | Goldstein et al. | 204/552 |
| 4,594,135 A | 6/1986 | Goldstein | 204/551 |
| 4,728,724 A | 3/1988 | Jones, Jr. et al. | 430/19 |
| 4,751,177 A | 6/1988 | Stabinsky | 435/6 |
| 4,787,963 A | 11/1988 | MacConnell | 204/450 |
| 4,804,625 A | 2/1989 | Morrison et al. | 435/7 |
| 4,816,418 A | 3/1989 | Mack et al. | 436/518 |
| 4,822,566 A | 4/1989 | Newman | 422/82 |
| 4,822,746 A | 4/1989 | Walt | 436/528 |
| 4,824,776 A | 4/1989 | Heller et al. | 435/6 |
| 4,859,583 A | 8/1989 | Heller et al. | 435/7 |
| 4,868,103 A | 9/1989 | Stavrianopoulos et al. | 435/5 |
| 4,908,112 A | 3/1990 | Pace | 210/198 |
| 4,996,143 A | 2/1991 | Heller | 435/6 |
| 5,063,081 A | 11/1991 | Cozzette et al. | 435/4 |
| 5,075,077 A | 12/1991 | Durley, III et al. | 422/56 |
| 5,096,807 A | 3/1992 | Leaback | 435/6 |
| 5,125,748 A | 6/1992 | Bjornson et al. | 356/414 |
| 5,126,022 A | 6/1992 | Soane et al. | 204/458 |
| 5,143,854 A | 9/1992 | Pirrung et al. | 436/518 |
| 5,164,319 A | 11/1992 | Hafeman et al. | 435/287 |
| 5,166,063 A | 11/1992 | Johnson | 435/173 |
| 5,200,051 A | 4/1993 | Cozzette et al. | 204/403 |
| 5,202,231 A | 4/1993 | Drmanac et al. | 435/6 |
| 5,219,726 A | 6/1993 | Evans | 435/6 |
| 5,227,265 A | 7/1993 | DeBoer et al. | 430/41 |
| 5,231,626 A | 7/1993 | Tadokoro et al. | 369/121 |
| 5,234,566 A | 8/1993 | Osman et al. | 204/403 |
| 5,278,051 A | 1/1994 | Seeman et al. | 435/91 |
| 5,304,187 A | 4/1994 | Wilding et al. | 435/29 |
| 5,312,527 A | 5/1994 | Mikkelsen et al. | 204/777 |
| 5,316,900 A | 5/1994 | Tsujioka et al. | 430/270 |
| 5,346,789 A | 9/1994 | Lewis et al. | 430/19 |
| 5,355,577 A | 10/1994 | Cohn | 29/592 |
| 5,380,833 A | 1/1995 | Urdea | 536/22 |
| 5,399,451 A | 3/1995 | Hashida et al. | 430/19 |
| 5,434,049 A | 7/1995 | Okano et al. | 435/6 |
| 5,505,700 A | 4/1996 | Leone et al. | |
| 5,561,043 A | 10/1996 | Cantor et al. | 435/6 |
| 5,565,322 A | 10/1996 | Heller | 435/6 |
| 5,637,458 A | 6/1997 | Frankel et al. | |
| 5,653,939 A | 8/1997 | Hollis et al. | 422/50 |
| 5,674,743 A | 10/1997 | Ulmer | 435/287 |
| 5,741,462 A | 4/1998 | Nova et al. | |
| 5,795,714 A | 8/1998 | Cantor et al. | |
| 5,965,410 A | * 10/1999 | Chen et al. | 435/91.2 |
| 5,972,187 A | 10/1999 | Parce et al. | |
| 6,033,546 A | 3/2000 | Ramsey | 204/603 |

FOREIGN PATENT DOCUMENTS

| | | |
|---|---|---|
| EP | 0229943 | 7/1987 |
| EP | 0617303 | 9/1994 |
| GB | 2156074 | 10/1985 |
| WO | WO 86/03782 | 7/1986 |
| WO | WO 88/08528 | 11/1988 |
| WO | WO 89/01159 | 2/1989 |
| WO | WO 89/10977 | 11/1989 |
| WO | WO 90/01564 | 2/1990 |
| WO | WO 92/04470 | 3/1992 |
| WO | WO 93/09128 | 5/1993 |
| WO | WO 93/21663 | 10/1993 |
| WO | WO 93/22678 | 11/1993 |
| WO | WO 95/07363 | 3/1995 |
| WO | WO 96/01836 | 1/1996 |

OTHER PUBLICATIONS

Anderson et al., "Quantitative Filter Hybridization", *Nucleic Acid Hybridization—A Practical Approach*. Eds. B.D.Hames & S.J.Higgins (Washington D.C.:IRL Press), 73–111 (1985).

Bains, "Setting A Sequence To Sequence A Sequence", *Bio/Technology*, 10, 757–758, Jul. 10, 1992.

Barinaga, "Will 'DNA Chip'Speed Genome Initiative?", *Science*, 253, 1489, Sep. 27, 1991.

Bauer et al., "Robotic Nanomanipulation With An SPM In A Networked Computing Environment", website printout, http://alicudi.usc.edu:80, 1–7, Nov. 20, 1997.

Beattie et al., The 1992 San Diego Conference: "Genosensor Technology", *Genetic Revolution*, 1–5, Nov. (1992).

Beltz et al., "Isolation Of Multigene Families & Determination Of Homologies By Filter Hybridization Methods", *Methods In Enzymology*, 100, 26–285 (1983).

Brown et al., "Electrochemically Induced Adsorption Of Radio–Labelled DNA On Gold & HOPG Substrates For STM Investigations". *Ultramicroscopy*, 38, 253–264 (1991).

Bugart et al., "Multiplex Polymerase Chain Reaction", *Modern Pathology*, 5, (3), 320–323, May, 1992.

Callahan et al., "Alignable Liftoff Transfer Of Device Arrays Via A Single Polymeric Carrier Membrane", *Electronics Letters*, 29, 951–953, May 27, 1993.

Cardullo et al., "Detection Of Nucleic Acid Hybridizations With Synthetic Olognucleotides", *Proc.Natl.Acad.Sci. USA*, 85, 8790–8794, Dec., 1988.

Connor et al., "Detection Of Sickle Cell $\beta^3$–Globin Allele By Hybridization With Synthetic Oligonucleotides". *Proc. .Natl.Acad.Sci. USA*, 80, 278–282, Jan., 1983.

Cuberes, "Room Temperature Repositioning Of Individual $C_{60}$ Molecules At Cu Steps: Operation Of A Molecular Counting Device", *Appl.Phys.Lett.*, 69, (20), 3016–3018 (1996).

Dagani, "Putting The Nano Finger On Atoms", *C& EN*, 20–23, Dec. 2, 1996.

Drmanac et al., "Sequencing Of Megabase Plus DNA By Hybridization: A Strategy For Efficient Large Scale Sequencing". *Genomics*, 4, 114–128 (1989).

Drmanac et al., "DNA Sequence Determination By Hybridization: A Strategy For Efficient Large Scale Sequencing". *Science*, 260, 1649–1652, Jun. 11, 1993.

Esener et al., "Punch–Through Current Under Diffusion Limited Injection: Analysis & Applications". *J.Appl.Phys.*, 12, 1380–1387, Aug., 1985.

Esener et al., "Design Considerations For Three–Terminal Optically Addressed MQW Spatial Light Modulators". Presented at The Annual Meeting Of OSA, at Seattle, Wash, Oct., 1986.

Esener et al., "One Dimensional Silicon/PLZT Spatial Light Modulators". *Opt.Eng.*, 26, (5), 406–413, (Also in: Proc.SPIE Annual Meeting In San Diego, 8/86), May, 1987.

Fan et al., "Fundamental Bandgap & Schottky Barrier Height Of Quarternary In AlGa As Grown On GaAs". MRS Meeting, Spring, 1992.

Fan et al., "Quantum–Confined Stark Effect Modulators At 1.06 $\mu$m On GaAs", accepted for publication, *IEEE Photonics Technology Letter*, 6, (12), 1383–1385, Dec., 1993.

Feldman et al., "A Comparison Of Electrical & Free Space Optical Interconnections" *Appl. Opt.*, 1742–1751 (1998).

Fodor et al., "Light Directed, Spatially Addressable Parallel Chemical Synthesis". *Science*, 251, 767–773 (1991).

Fodor et al., "Multiplexed Biochemical Assays With Biological Chips". *Nature*, 364, 555–556 (1993).

Garner et al., "Absorption Detection In Capillary Electrophoresis By Fluorescence Energy Transfer". *Anal.Chemistry*, 62, (2), 2193–2198, Oct. 15, 1990.

Glazer et al., "Emerging Techniques Physofluor Probes", *Trends In Biochemical Sciences*, 9, (10), 423–427.(1984).

Haddon et al., "The Molecular Electronic Device & The Biochip Computer: Present Status", *Proc.Natl.Acad.Sci.USA*, 82, 1874–1878 (1985).

Halfhill, "New Memory Architectures To Boost Performance", *Byte*, 86–87, Jul., 1993.

Heller, "An Active Microelectronics Device For Multiplex DNA Analysis", *IEEE Engineering In Medicine & Biology*, 15, (2), 100–104, Mar.–Apr., 1996.

Heller et al., "Interaction Of Divalent Manganese Ion With Adenosine Triphosphate & Related Compounds", *Biochemistry*, 9, (25), 4970 (1970).

Heller et al., "Interactions Of Miracil D With Double–Stranded Polyadenylic Acid & Polyuridylic Acid", *Biochemistry*, 13, 1623 (1974).

Heller et al., *Rapid Detection & Infection Of Infectious Diseases*. Eds. Kingsbury et al. (New York: Academic Press), 245–256 (1986).

Heller et al., "Chemiluminescent & Fluorescent DNA Probes In Hybridization Systems", *Rapid Detection & Identification Of Infectious Agents*. Eds. Kingsbury et al. (New York: Academic Press), 345–365 (1985).

Heller et al., "Self–Organizing Structures Based On Functional Synthetic Nucleic Acid Polymers", *Nanotechnology*, 2, 165–171 (1991).

Heller et al., "Microelectrophoresis For The Separation Of DNA Fragments", *Electrophoresis*, 13, 512–520 (1992).

Heller et al., "Fluorescent Detection Methods In PCR Analysis", *The Polymerase Chain Reaction*. Eds. Mullis et al. (Birkhanuser) (1994).

Hopfield et al., "A Molecular Shift Register Based On Electron Transfer", *Science*, 241, 817–820, Aug. 12, 1988.

Horejsí et al., "Some Theoretical Aspects Of Affinity Electrophoresis", *Jnl. Of Chromatography*, 1–13 (1979).

Horejsí et al., "Determination Of Dissociation Constants Of Lectin Sugar Complexes By Means Of Affinity Electrophoresis", *Biochemica et Biophysica Acta*, 499, 290–300 (1977).

Iakoubova et al., "Oncogene Amplification Screening By Labeled Primer Multiiplex Polymerase Chain Reaction", *Modern Pathology*, 7, (7), 784–789, Sep., 1994.

Keller et al., *DNA Probes*. (New York: Stockton Press), 104–108 (1989).

Kornberg, *DNA Synthesis*. Eds. William H. Freeman (San Francisco) (1974).

Krishnakumar et al., "Deposition Characterization Of Thin Ferroelectric Lead Lanthaum Zircontate Titanate (PLTZ) Films On Sapphire For Spatial Light Modulators Applications", *IEEE Transactions On Ultrasonics, Ferroelectrics & Frequency Control*, 38, (6), 585–590, Nov., 1991.

Lee et al., "Interfacial Properties Of InAlAs/InGaAs High FETs & MIS Capacitors", *Semiconductor Science & Technology*, 5, 716–720 (1990).

Lin et al., "Two Dimensional Spatial Light Modulators Fabricated In Si/PLZT", *Appl.Opt*, 29, (11), Apr., 1990.

Mansoonian et al., "A Comparison Of Transmitter Technologies For Digital Free–Space Optical Interconnection", Submitted To *Applied Optics*, Jul., 1994.

McAlear et al., *Molecular Electronic Devices II*. Eds. Carter (New York: Marcel Dekker), 623–633 (1987).

Mizuno, The Organic Chemistry Of Nucleic Acids (Tokyo: Elsevier), 181–200 (1986).

Morrison et al., "Solution Phasing Detection Of Polynucleotides Using Interacting Fluorescent Labels & Competitive Hybridization", *Anal.Biochem.*, 183, 231–244 (1989).

Moses, "Bioelectronics: Biochips", *Biotechnology: The Science & The Business*, ch 21, 371–378 (1991).

Niemeyer, "DNA As A Material For Nanotechnology", *Angew Chem.Int.Ed.Engl.*, 36, 585–587 (1997).

Palecek, "New Trends In Electrochemical Analysis Of Nucleic Acids", *Bioelectrochemistry & Bioenergetics*, 20, 179–194 (1988).

Ranki et al., "Sandwich Hybridization As A Convenient Method For Detection Of Nucleic Acids In Crude Samples", *Gene*, 21, 77–85 (1983).

Requicha, "Nanorobotics", web site printout, http://alicudi.usc.edu:80, 1–13, Nov. 20, 1997.

Robinson et al., "The Design Of A Biochip: A Self–Assembling Molecular Scale Memory Device", Protein Eng., 1, 295–300 (1987).

Saiki, "Amplification Of Genomica DNA", *PCR Protocols: A Guide To Methods & Applications*. (Academic Press), 13–20 (1990).

Shih et al., "Quantum–Confined Stark Effective Modulatos On GaAs Substrates", *Electronic Letters*, 30, (20), Sep., 1994.

Shih et al., "Integration Of InAlGaAs./InGaAs MODFET's On MQW Modulators On GaAs Substrates", *Electronic Letters*, 30, (20), Sep., 1994.

Southern et al., "Analyzing & Comparing Nucleic Acid Sequences By Hybridization To Arrays Of Oligonucleotides Evaluation Using Experimental Models", *Genomics*, 13, 1008–1017 (1992).

Stezoska et al., "DNA Sequencing By Hybridization: 100 Bases Ready By A Non–gel Based Method", *Proc.Natl.Acad.Sci. USA*, 88, 10089–10093 (1991).

Stroscio et al., "Atomic & Molecular Manipulation With The Scanning Tunneling Microscope", *Science*, 254, 1319–1326 (1991).

Tu et al.., "Structure & Stability Of Metal Nucleoside Phosphate Complexes", *Metal Ions & Biological System*, 1, chap 1., Eds. Siegal (New York: Marcel Dekker) (1974).

Uchida et al., "Single Atom Manipulation On The Si(III) 7x7 Surface By The Scanning Tunneling Microscope (STM)". *Surface Science*, 287/288, 1056–1061 (1993).

Wallace et al., "Hybridization of Synthetic Oligodeoxyribonucleotides To φ x 174 DNA: The Effect Of Single Base Pair Mismatch", *Nucleic Acid Res.* 6, (11), 3543–3557 (1979).

Washizu, "Electrostatic Manipulation Of Biological Objects", *Journal of Electrostatics*, 25, 109–123 (1990).

Washizu, "Electrostatic Manipulation Of DNA In Microfabricated Structures", *IEEE Transactions On Industry Applications*, 26, (6), 1165–1172, Nov.–Dec., 1990.

Whitesides et al., "Molecular Self–Assembly & Nanochemistry: A Chemical Synthesis Of Nanostructures". *Science*, 254, 1312–1318 (1994).

Wilke et al., "Use Of Thiazole Orange Homodimer As An Alternative To Ethidium Bromide For DNA Detection In Agarose Gels", *Modern Pathology*, 7, (3), 385–387, Apr., 1994.

Yu et al., "A Novel In GaAs PIN Photodiode On Semi–Insulating InP", *Optical & Quantum Electronics*, 18, 174–176 (1986).

Yu et al., "Self Aligned Diffusion Technique For N–Imp JFETS", *Electron Lett*, 23, 981–982, 1987.

* cited by examiner

METHODS APPARATUS FOR THE ELECTRONIC, HOMOGENEOUS ASSEMBLY AND FABRICATION OF DEVICES

RELATED APPLICATION INFORMATION

This application is a continuation-in-part application of application Ser. No. 08/760,933, filed Dec. 6, 1996, entitled "Affinity Based Self-Assembly Systems and Devices for Photonic and Electronic Applications", which is a continuation-in-part application of application Ser. No. 08/534,454, filed Sep. 27, 1995, entitled "Apparatus and Methods for Active Programmable Matrix Devices", now issued as U.S. Pat. No. 5,849,486, which is a continuation-in-part of application Ser. No. 08/304,657, filed Sep. 9, 1994, entitled, as amended, "Molecular Biological Diagnostic Systems Including Electrodes", now issued as U.S. Pat. No. 5,632,957, which is a continuation-in-part of application Ser. No. 08/271,882, filed Jul. 7, 1994, entitled, as amended, "Methods for Electronic Stringency Control for Molecular Biological Analysis and Diagnostics", now issued as U.S. Pat. No. 6,017,696, which is a continuation-in-part of application Ser. No. 08/146,504, filed Nov. 1, 1993, entitled, as amended, "Active Programmable Electronic Devices for Molecular Biological Analysis and Diagnostics", now issued as U.S. Pat. No. 5,605,662, application Ser. No. 08/703,601, filed Aug. 23, 1996, entitled "Hybridization of Polynucleotide Conjugated with Chromophores and Fluorophores to Generate Donor-to-Donor Energy Transfer System", now issued as U.S. Pat. No. 5,849,489, which is a continuation of Application Ser. No. 08/232,233, filed May 5, 1994, entitled "Hybridization of Polynucleotide Conjugated with Chromophores and Fluorophores to Generate Donor-to-Donor Energy Transfer System", now issued as U.S. Pat. No. 5,565,322, which is a continuation-in-part of application Ser. No. 07/790,262, filed Nov. 7, 1991, entitled "Self-Organizing Molecular Photonic Structures Based on Chromophore- and Fluorophore-Containing Polynucleotide and Methods of Their Use", now issued as U.S. Pat. No. 5,532,129 (via continuation application Ser. No. 08/250,951, filed May 27, 1994), application Ser. No. 09/129,470, entitled "DNA Optical Storage Memory", filed Aug. 5, 1998, now issued as U.S. Pat. No. 6,329,143, which is a continuation of application Ser. No. 08/906,569, Aug. 5, 1997, entitled "Optical Storage Device Utilizing Non-Radiative Energy Transfer" now issued as U.S. Pat. No. 5,835,404, which is a continuation of application Ser. No. 08/258,168, filed June 10, 1994, entitled "DNA Optical Storage", now issued as U.S. Pat. No. 5,787,032, and application Ser. No. 08/968,065, entitled "Methods and Procedures for Molecular Biological Analysis and Diagnostics", filed Dec. 5, 1997, now issued as U.S. Pat. No. 6,029,764, which is a continuation-in-part of application Ser. No. 08/855,058, entitled "Methods for Electronic Perturbation Analysis of Biological Materials", filed May 14, 1997, now issued as U.S. Pat. No. 6,048,690, all incorporated herein by reference as if fully set forth herein.

FEDERAL FUNDS STATEMENT

This invention was made with Government support under Contract F30602-97-C-0155 awarded by the Air Force. The Government has certain rights in this invention.

FIELD OF THE INVENTION

This invention relates to methodologies and techniques for the design, fabrication and use of a fluidic system incorporating means by which electric fields are applied to carry out the assembly of micron to nanoscale materials. By way of example, the inventions serve to form microelectronic, micromechanical, microoptical and mixed function devices or assemblies both in two dimensions and three dimensions. This invention also relates to associated microelectronic and optoelectronic devices, systems, and manufacturing platforms which provide electric field transport, and optionally, selective addressing of components, including self-assembling, nanostructures, submicron and micron sized components to selected locations on the device itself or onto other substrate materials.

BACKGROUND OF THE INVENTION

The fields of molecular electronics/photonics and nanotechnology offer immense technological promise for the future. Nanotechnology is defined as a projected technology based on a generalized ability to build objects to complex atomic specifications. Drexler, *Proc. Natl. Acad. Sci USA*, 78:5275–5278, (1981). Nanotechnology generally means an atom-by-atom or molecule-by-molecule control for organizing and building complex structures all the way to the macroscopic level. Nanotechnology is a bottom-up approach, in contrast to a top-down strategy like present lithographic techniques used in the semiconductor and integrated circuit industries. The success of nanotechnology may be based on the development of programmable self-assembling molecular units and molecular level machine tools, so-called assemblers, which will enable the construction of a wide range of molecular structures and devices. Drexler, "Engines of Creation," Doubleday Publishing Co., New York, N.Y. (1986).

Present molecular electronic/photonic technology includes numerous efforts from diverse fields of scientists and engineers. Carter, ed., "Molecular Electronic Devices II," Marcel Dekker, Inc, New York, N.Y. (1987). Those fields include organic polymer based rectifiers, Metzger et al., "Molecular Electronic Devices II," Carter, ed., Marcel Dekker, New York, N.Y., pp. 5–25 (1987), conducting conjugated polymers, MacDiarmid et al., *Synthetic Metals*, 18:285 (1987), electronic properties of organic thin films or Langmuir-Blogett films, Watanabe et al., *Synthetic Metals*, 28:C473 (1989), molecular shift registers based on electron transfer, Hopfield et al., *Science*, 241:817 (1988), and a self-assembly system based on synthetically modified lipids which form a variety of different "tubular" microstructures. Singh et al., "Applied Bioactive Polymeric Materials," Plenum Press, New York, N.Y., pp. 239–249 (1988). Molecular optical or photonic devices based on conjugated organic polymers, Baker et al., *Synthetic Metals*, 28:D639 (1989), and nonlinear organic materials have also been described. Potember et al., *Proc. Annual Conf. IEEE in Medicine and Biology*, Part 4/6:1302–1303 (1989).

However, none of the cited references describe a sophisticated or programmable level of manufacturing self-organization or self-assembly. Typically, the actual molecular component which carries out the electronic and/or photonic mechanism is a natural biological protein or other molecule. Akaike et al., *Proc. Annual Conf. IEEE in Medicine and Biology*, Part 4/6:1337–1338 (1989). There are presently no examples of a totally synthetic programmable self-assembling molecule which produces an efficient electronic or photonic structure, mechanism or device.

Progress in understanding self-assembly in biological systems is relevant to nanotechnology. Drexler, *Proc. Natl. Acad. Sci USA*, 78:5275–5278 (1981), and Drexler, "Engines of Creation," Doubleday Publishing Co., New York, N.Y. (1986). Areas of significant progress include the organization of the light harvesting photosynthetic systems, the energy transducing electron transport systems, the visual process, nerve conduction and the structure and function of the protein components which make up these systems. The so-called bio-chips described the use of synthetically or biologically modified proteins to construct molecular electronic devices. Haddon et al., *Proc. Natl. Acad. Sci. USA*, 82:1874–1878 (1985), McAlear et al., "Molecular Electronic Devices II," Carter ed., Marcel Dekker, Inc., New York N.Y., pp. 623–633 (1987).

Some work on synthetic proteins (polypeptides) has been carried out with the objective of developing conducting networks. McAlear et al., "Molecular Electronic Devices," Carter ed., Marcel Dekker, New York, N.Y., pp. 175–180 (1982). Other workers have speculated that nucleic acid based bio-chips may be more promising. Robinson et al., "The Design of a Biochip: a Self-Assembling Molecular-Scale Memory Device," *Protein Engineering*, 1:295–300 (1987).

Great strides have also been made in the understanding of the structure and function of the nucleic acids, deoxyribonucleic acid or DNA, Watson, et al., in "Molecular Biology of the Gene," Vol. 1, Benjamin Publishing Co., Menlo Park, Calif. (1987), which is the carrier of genetic information in all living organisms (See FIG. 1). In DNA, information is encoded in the linear sequence of nucleotides by their base units adenine, guanine, cytosine, and thymidine (A, G, C, and T). Single strands of DNA (or polynucleotide) have the unique property of recognizing and binding, by hybridization, to their complementary sequence to form a double stranded nucleic acid duplex structure. This is possible because of the inherent base-pairing properties of the nucleic acids: A recognizes T, and G recognizes C. This property leads to a very high degree of specificity since any given polynucleotide sequence will hybridize only to its exact complementary sequence.

In addition to the molecular biology of nucleic acids, great progress has also been made in the area of the chemical synthesis of nucleic acids. This technology has developed so automated instruments can now efficiently synthesize sequences over 100 nucleotides in length, at synthesis rates of 15 nucleotides per hour. Also, many techniques have been developed for the modification of nucleic acids with functional groups, including: fluorophores, chromophores, affinity labels, metal chelates, chemically reactive groups and enzymes. Smith et al., *Nature*, 321:674–679 (1986); Agarawal et al., *Nucleic Acids Research*, 14:6227–6245 (1986); Chu et al., *Nucleic Acids Research*, 16:3671–3691 (1988).

An impetus for developing both the synthesis and modification of nucleic acids has been the potential for their use in clinical diagnostic assays, an area also referred to as DNA probe diagnostics. Simple photonic mechanisms have been incorporated into modified oligonucleotides in an effort to impart sensitive fluorescent detection properties into the DNA probe diagnostic assay systems. This approach involved fluorophore and chemilluminescent-labeled oligonucleotides which carry out Förster nonradiative energy transfer. Heller et al., "Rapid Detection and Identification of Infectious Agents," Kingsbury et al., eds., Academic Press, New York, N.Y. pp. 345–356 (1985). Förster nonradiative energy transfer is a process by which a fluorescent donor group excited at one wavelength transfers its absorbed energy by a resonant dipole coupling process to a suitable fluorescent acceptor group. The efficiency of energy transfer between a suitable donor and acceptor group has a $1/r^6$ distance dependency (see Lakowicz et al., "Principles of Fluorescent Spectroscopy," Plenum Press, New York, N.Y., Chap. 10, pp. 305–337 (1983)).

As to photonic devices, they can generally be fabricated in dense arrays using well developed micro-fabrication techniques. However, they can only be integrated over small areas limited by the relatively high defect densities of the substrates employed. In order to be useful and economically viable, these devices must in many cases, be used within large area silicon integrated circuits. A good example of this issue is the vertical cavity surface emitting lasers. To address many potential applications, it would be highly desirable to integrate these devices with large area silicon IC's. A major obstacle in the integration of these new devices with silicon is the existence of material and geometrical incompatibilities. These devices need to be integrated on silicon in large sparse arrays with minimal performance degradation, and without affecting the underlying silicon circuits. Over the past years, a number of component assembly technologies have been extensively investigated regarding the integration of such compound semiconductor devices on silicon. These include hybrid flip-chip bonding or epitaxial lift-off and other direct bonding methods. Although these hybrid technologies have made significant progress and several component demonstrations have shown the viability of these techniques, these methods do not address the problem of geometrical incompatibility. That is, the dimensions with which the specialty devices are fabricated on their mother substrate must be conserved when they are coupled onto the host substrate. This makes the integration of small area devices on large area components economically unfeasible.

A major obstacle in the integration of these new devices with silicon is the existence of material and geometrical incompatibilities. These devices need to be integrated on silicon in large sparse arrays with minimal performance degradation, and without affecting the underlying silicon circuits. Over the past years, a number of component assembly technologies have been extensively investigated regarding the integration of such compound semiconductor devices on silicon. These include hybrid flip-chip bonding or epitaxial lift-off and other direct bonding methods. Although these hybrid technologies have made significant progress and several component demonstrations have shown the viability of these techniques, these methods do not address the problem of geometrical incompatibility. That is, the dimensions with which the specialty devices are fabricated on their mother substrate must be conserved when they are coupled or grafted onto the silicon board.

Efforts have been made to fabricate self-assembling microstructures onto a substrate through fluid transport. For example, in U.S. Pat. No. 5,783,856, entitled "Method for Fabricating Self-Assembling Microstructures", methods and apparatus are disclosed which utilized microstructures having shaped blocks which self-align into recessed regions located on a substrate such that the microstructure becomes integral with the substrate. A slurry containing multiple devices is then poured over the substrate bearing the recessed regions such that the microstructures selectively engage with the substrate.

The prior art has no integration technique that is capable of creating a sparse array of devices distributed over a large area, when the devices are originally fabricated densely over small areas. This makes large area components made up from integration of micron size devices economically unfeasible. To solve this problem, the electronics industry employs a hierarchy of packaging techniques. However, this problem remains unsolved when a regular array of devices is needed on large areas with a relatively small pitch. This problem is probably most noticeable through the high cost associated with the implementation of matrix addressed displays, where the silicon active matrix consists of small transistors that need to be distributed over a large area. Thus, prior art microfabrication techniques limit devices to small area components where a dense array of devices are integrated. However, there are a number of important applications that could benefit from specialty devices being integrated more sparsely over large areas.

One possible method for removing the geometrical limitations is the further development of semiconductor substrate materials to the point where their defect densities approaches that of silicon. This is a long and expensive process that requires incremental progress. A second approach is the development of special robots capable of handling micron and sub-micron size devices and able to graft them to appropriate places. This also seems impractical because the grafting process will remain sequential where one device may be grafted after another, requiring impractical processing times. In any case, both of these approaches may be limited to motherboard dimensions on the order of 10 cm.

With regard to memories, data processing engines have been physically and conceptually separated from the memory which stores the data and program commands. As processor speed has increased over time, there has been a continuous press for larger memories and faster access. Recent advances in processor speed have caused system bottlenecks in access to memory. This restriction is critical because delays in obtaining instructions or data may cause significant processor wait time, resulting in loss of valuable processing time.

Various approaches have been taken to solve these concerns. Generally, the solutions include using various types of memory which have different attributes. For example, it is common to use a relatively small amount of fast, and typically expensive, memory directly associated with the processor units, typically called cache memory. Additionally, larger capacity, but generally slower, memory such as DRAM or SRAM is associated with the CPU. This intermediate memory is often large enough for a small number of current applications, but not large enough to hold all system programs and data. Mass storage memory, which is ordinary very large, but relatively inexpensive, is relatively slow. While advances have been continually made in improving the size and speed of all types of memory, and generally reducing the cost per bit of memory, there remains a substantial need especially to serve yet faster processors.

For the last 20 years most mass storage devices have utilized a rotating memory medium. Magnetic media have been used for both "floppy" (flexible) disks or "hard" disk drives. Information is stored by the presence or absence of magnetization at defined physical locations on the disk. Ordinarily, magnetic media are "read-write" memories in that the memory may be both written to and read from by the system. Data is written to or read from the disk by heads placed close to the surface of the disk.

A more recent development in rotating mass storage media are the optical media. Compact disks are read only memory in which the presence or absence of physical deformations in the disk indicates the data. The information is read by use of a focused laser beam, in which the change in reflectance properties from the disk indicate the data states. Also in the optical realm are various optical memories which utilize magnetooptic properties in the writing and reading of data. These disks are both read only, write once read many ("WORM") drives and multiple read-write memories. Generally, optical media have proved to have a larger storage capacity, but higher costs per bit and limited write ability, as compared with magnetic media.

Several proposals have been made for using polymers for electronic based molecular memories. For example, Hopfield, J. J., Onuchic, J. N. and Beratan, D. N., "A Molecular Shift Register", Science, 241, p. 817, 1988, discloses a polymer based shift register memory which incorporates charge transfer groups. Other workers have proposed an electronic based DNA memory (see Robinson et al, "The Design of a Biochip: A Self-Assembling Molecular-Scale Memory Device", Protein Engineering, 1:295–300 (1987)). In this case, DNA is used with electron conducting polymers for a molecular memory device. Both concepts for these molecular electronic memories do not provide a viable mechanism for inputting data (write) and for outputting data (read).

Molecular electronic memories have been particularly disappointing in their practical results. While proposals have been made, and minimal existence proofs performed, generally these systems have not been converted to commercial reality. Further, a specific deficiency of the system described above is that a sequential memory is typically substantially slower than a random access memory for use in most systems.

The optical memories described above suffer from the particular problem of requiring use of optical systems which are diffraction limited. This imposes size restrictions upon the minimum size of a data bit, thereby limiting memory density. This is an inherent limit in systems which store a single bit of data at a given physical memory location.

Further, in all optical memory systems described above, the information is stored on a bit-by-bit basis, such that only a single bit of data is obtained by accessing a giving physical location in memory. While word-wide memory access systems do exist, generally they store but a single bit of information at a given location, thereby requiring substantially the same amount of physical memory space whether accessed in a bit manner or word-wide manner.

While systems have generally increased in speed and storage density, and decreased in cost per bit, there remains a clear gap at present between processor speed and system requirements. See generally, "New Memory Architectures to Boost Performance", Tom R. Halfhill, Byte, July, 1993, pp. 86 and 87. Despite the general desirability of memories which are faster, denser and cheaper per bit, and the specific critical need for mass memory which can meet the demands of modem day processor systems speed, no completely satisfactory solution has been advanced heretofore. The fundamental limitations on the currently existing paradigms cannot be overcome by evolutionary enhancements in those systems.

Despite the clear desirability for new and improved apparatus and methods in this field, no optimal solution has been proposed previously.

SUMMARY OF THE INVENTION

Increasingly, the technologies of communication, information processing, and data storage are beginning to depend upon highly-integrated arrays of small, fast electronic and photonic devices. As device sizes scale down and array sizes increase, conventional integration techniques become increasingly costly. The dimensions of photonic and electronic devices permit the use of electronic assembly and/or molecular biological engineering for the integration and manufacturing of photonic and electronic array components. This invention also relates to associated microelectronic and optoelectronic devices, systems, and manufacturing platforms which provide electric field transport and selective addressing of self-assembling, nanostructures, sub-micron and micron size components to selected locations on the device itself or onto other substrate materials.

More broadly, the invention in this respect relates to a method for the fabrication of micro scale and nanoscale devices comprising the steps of fabricating first component devices on a first support, releasing at least one first component device from the first support, transporting the first component device to a second support, and attaching the first component device to the second support. In particular, electrostatic, electrophoretic and electroosmotic forces may be employed to transport,,position and orient components upon a suitably designed substrate either in sequential steps or in parallel. Optionally, nucleic acid hybridization or other forms of molecular biological or other forms of reversibly binding systems may be employed to promote self-assembly and self-sorting of materials as components within or between components of these assemblies. A further aspect of this invention involves carrying out the various electric filed assisted assembly processed under low gravity conditions, which may improved the overall performance.

This invention relates to the means of enabling micron and nanoscale assembly in a fluid medium by use of electric fields for placement of components and subassemblies. This invention also encompasses the design, composition and manufacture of components, assembly substrates or platforms and component delivery systems as well as the composition of the fluid medium. This technology lends itself to scaling dimensions ranging from the molecular (sub-nanometer) to the micron. Furthermore, the use of self-organizing or self-assembling molecules such as polynucleic acids can serve to augment the overall utility of this approach. This broad flexibility is unique to this technology and represents a novel application of electric fields, devices and materials. The heterogeneous assembly of microelectronic, microoptical and micromechanical components upon an integrated silicon circuit represents one such use of this approach. Thus, this invention relates to the employment of electric fields, the nature and scale of materials to be assembled, the electrical and chemical properties of the assembly surface or environment, the means by which electrical interconnects may be formed and the potential utility of such assembled devices.

The electric fields relating to this invention can be either electrostatic, electrophoretic, electroosmotic, or dielectrophoretic in nature. In addition, the resultant forces used for component positioning may be comprised of various combinations of these. In application, a fluid medium, typically aqueous in composition, would be deposited onto the assembly surface. This surface has one or more microlocations which govern the application of these electric fields through the fluid medium. Devices or components for assembly are added to the fluid medium and then are targeted by control of the electric fields to defined positions upon the assembly surface. Transport is accomplished by interactions between the device and the nature and effects of the forces engendered by the electric fields. In particular, if net charges are present upon the components or devices, electrophoretic or possibly electrostatic forces would be factors governing movement of the materials. Alternatively, if no net charge is present upon these materials, forces such as electroosmosis which enables bulk fluid movement or dielectrophoresis may be employed to maneuver and locate the devices at specific locations upon the surface. In certain circumstances, both electrophoretic and electroosmotic (or other combinations of forces) may work in combination to guide position and orientation of component assembly.

The use of electric fields has been described for the movement of biological molecules, typically nucleic acids or proteins, for the purpose of analysis, diagnosis or separation. See, e.g., U.S. Pat. No, 5,605,662. These inventions are more particularly directed to the assembly of micron to sub-micron to nano-scale assembly of components to form functional composite devices or sub-assemblies. Such heterogeneous integration using these fields represents a novel means by which assembly technology can progress to new dimensions and materials. One advantage of this non-mechanical "pick-and-place" assembly technology is the ability to handle a variety of component shapes and sizes upon a common platform. In addition, the forces employed are self-governing in so far as the movement of the components is regulated by the components themselves, i.e. their shape, their dimensions and their surface charge and not dependent upon an external mechanical device. This feature thereby lessens or minimizes the likelihood of possible mechanical damage to possibly fragile components during placement.

Key to the utilization of this technology is an appropriately designed and composed assembly platform. Such a platform contains electrodes on the assembly surface enabling the formation of electric fields that establish the forces necessary for transport of devices and components during the assembly process. These electrodes may either be at the point to which the components are to be located or adjacent to these locations (i.e. "drive" electrodes). The latter form of electrodes would typically not serve as electrical connection points to the assembly, but rather as aids to the assembly process. Other electrodes may serve both roles, operating both as driving points for assembly and as locations for electrical contact between the components and the underlying assembly platform. Combinations of both drive electrodes and "contact" electrodes may be present at any one assembly location or throughout the assembly platform.

Also, the surface of the assembly platform may be adopted or modified through lithographic techniques to present stop points or recesses into which the components can be electronically positioned. These arresting points by themselves are constructed such that, in the absence of applied electronic control, movement of devices and components as well as their orientation at these positions would not be possible.

The composition of the assembly surface is also modifiable in order to more precisely match the needs of the assembly process. In particular, the surface can be covered with a permeable layer composed of hydrogels, SiO2, or other related materials suitable for providing sites of attachment for molecules useful for anchoring devices, components, nanoscale and molecular scale materials as well as serving as a means of distancing the assembly site from the reactive zone set up when electrolysis of water occurs.

The other form of coating would be one which modifies the inherent charge of the surface and velocity of fluid, either augmenting, neutralizing or reversing electroosmotic flow along this surface. In contrast to the permeation layer whose functionality and role is useful at or adjacent to working electrodes, this surface modifying coat would be functioning not at the active electrodes per se but at the assembly surface between electrode locations.

A new class of components or devices would be designed for use with this system. That is, these components would contain features both enabling derivatization with suitable chemistry in order to provide charge and/or sites of attachment for molecules providing charge and/or self-assembly functionality, e.g. nucleic acids, and would be constructed in such a fashion as to provide contact features enabling electric connection between the component and either the underlying assembly platform or other devices or materials attached to this component itself. Contacts could be so constructed as to remove the need for specific orientation of the device on the assembly platform. That is, by use of concentric ring electrodes on the component device, the need to orient the device upon the assembly platform is removed by having an infinite number of orientations while in that plane being suitable. Alternatively, the outside faces of the component or device might be shaped such as to enable locating into modified assembly surface features, e.g., use of matching shaped devices with corresponding surface depressions or stops. Such designs would serve to provide alignment of electrical and mechanical contacts for the devices and components to the assembly platform and to other components, devices, and sub-assemblies.

An important feature would the mechanism to deliver components and materials to the assembly platform. A microfluidic delivery head comprised of both the means to contain components prior to application to the working platform and the counter electrode necessary to set the appropriate electric field geometry aiding assembly is one such design that may be employed. Each of these two aspects represents novel application (and modification) of existing technology, e.g. microfluidics and electrode design. In addition, the means of fluidic delivery itself may be combined with the counter electrode such that devices are either electrophoretically or electroosmotically transported through the device head into fluid overlaying the assembly platform. In an alternative embodiment, a device platform may receive a motherboard and provide the return electrode or conduction path for electrode sites on the motherboard. In this way, the number of electrodes on the motherboard may be reduced, and the device simplified. The device platform may contain sources of component devices, such as substrates from which component devices are subject to lift-off.

Electrical or mechanical connections between assembled components may take place either serially, as each set of components is arranged or as a final step in the assembly process. These connections depend in part upon the surfaces to be joined and the type of joint to be formed. In particular, we have discovered that metals can be electrodeposited through permeation layers to form electrical contact to materials positioned at these locations. In addition, conductive materials, e.g. organic polymers, could be used to coat the polynucleotide scaffolding employed for self-assembly.

Some potential applications for these techniques are: (1) Fabricating light emitter arrays over large surfaces; (2) assembly of two or three-dimensional photonic crystal structures; (3) two and three dimensional high density data storage materials, devices and systems; and (4) manufacturing of various hybrid-integrated components including flat panel displays, wireless/RF integrated devices, lab on a chip devices, microcantiliver sensor devices, atomic force microscope devices, integrated MEMS/optical/microelectronic devices, integrated microscopic analytical and diagnostic devices, and compact/handheld medical diagnostic devices and systems.

As photonics plays an increasingly important role in information processing, communication and storage systems it will deliver faster, smaller, more power efficient, and functionally versatile integrated systems at lower cost. New fabrication technologies including nanostructure fabrication, integration and self-assembly techniques are used. As device dimensions shrink to submicron levels, it becomes important to utilize the inventive concepts employing molecular biological engineering concepts and principles as manufacturing techniques for the fabrication of integrated photonic and electronic devices.

In one particular implementation, light emitting diodes (LEDs) may be fabricated on a support and removed therefrom utilizing a lift-off technique. Component devices such as the LEDs may then be placed on the motherboard or target device generally in the target position through use of electroosmotic force. Once the component device has been appropriately placed, substantially permanent electrical contact with the motherboard or target device is then effected. In the preferred embodiment, the component device is subject to a soldering technique, such as through a solder reflow technique.

In yet another aspect of this invention, methods for the assembly of devices in a low gravity environment are provided. More particularly, electrical transport, preferably electrostatic or electrophoretic, but also possibly electroosmotic or dielectrophoretic, may be utilized in a low gravity environment to place devices from a source of devices onto target structures or motherboards and to then affixed and activate those devices on that target device or motherboard.

Accordingly, it is one object of this invention to enable micron and sub-micron (including nanotechnology) through use of electrical transport and placement of component devices from a source to target locations, and to affix and, if required by the nature of the device, to activate the device through cooperation with the target device or motherboard.

In yet another aspect, these inventions seek to employ electrical forces, such as electrostatic, electrophoretic and electroosmotic forces, to transport, position and orient components upon a designed substrate.

In yet another aspect of this invention, the methods and apparatus are designed to optimally provide parallel actions, such as through the parallel transport of various component devices to multiple target locations.

It is an object of this invention to enable nanotechnology and self-assembly technology by the development of programmable self-assembling molecular construction units.

Figure 1B:
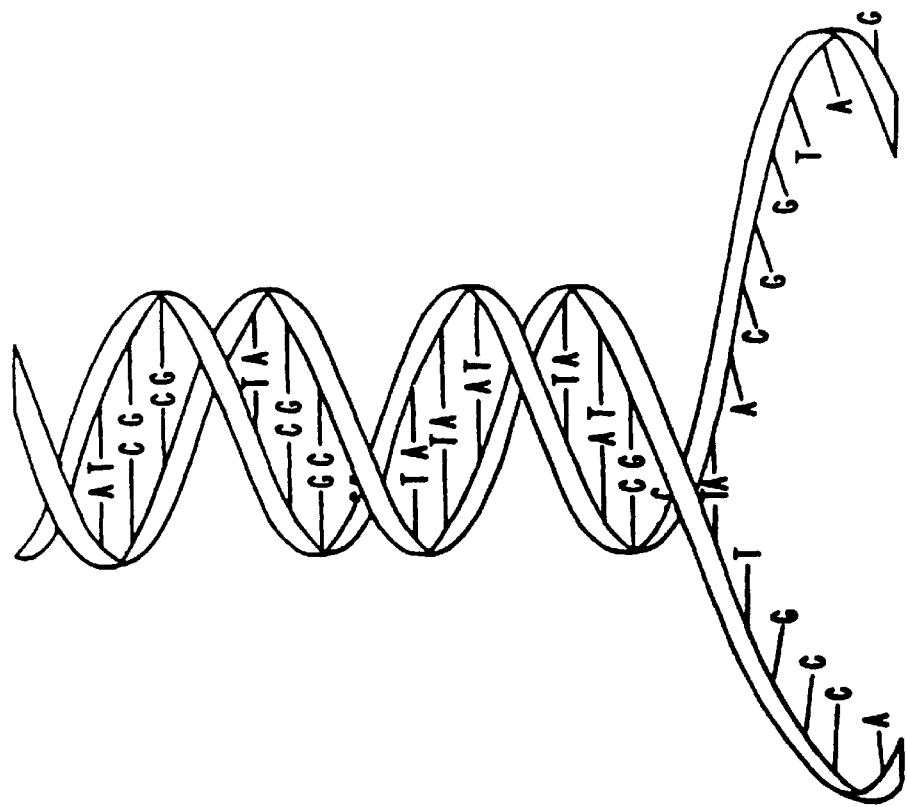
FIGS. 1A and 1B show DNA structure and its related physical dimensions.
Figure 1A:
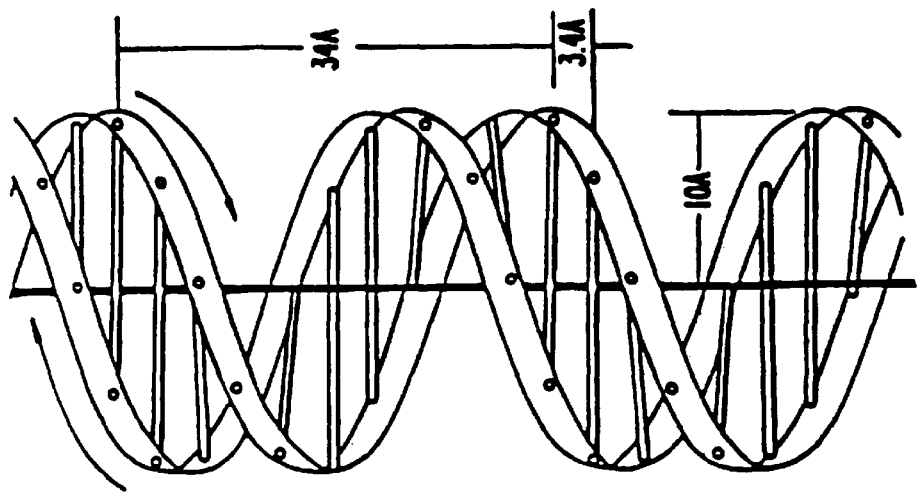

Important Aspects of DNA Structure, Properties, and Synthesis

Synthetic DNA possesses a number of important properties which make it a useful material for the applications of these inventions. The most important are the molecular recognition (via base pairing) and self-assembly (via hybridization) properties which are inherent in all DNA molecules. Other important advantages include the ability to easily synthesize DNA, and to readily modify its structure with a variety of functional groups. We have extensively investigated the photonic and electronic energy transfer mechanisms in self-assembled arrangements of synthetic DNA functionalized with a wide variety of donor and acceptor chromophore groups. We have paid particular attention to the basic problems involved in communicating or getting information in and out of these molecular structures. This basic work is now being applied to potential applications for high density optical storage materials, which have been designed to absorb light energy at a single wavelength and re-emit at predetermined multiple wavelengths. We are also now using DNA polymers for the two and three dimensional organization of micron and submicron sized structures on silicon surfaces. This work is being directed at the development of novel optoelectronic devices.

The DNA molecule is considered important to certain aspects of this invention and the proposed applications because it is inherently programmable and can self-assemble. Designing, synthesizing, and organizing these systems requires nanometer range control which few other synthetic polymer systems can match. Additionally, DNA molecules are relatively stable and have a number of other attributes which make them a preferred material for nanofabrication.

The underlying technology for DNA and other nucleic acid type polymers comes from the enormous effort that has been invested over the past fifteen years in synthetic nucleic acid chemistry. Molecular biologists have refined techniques and DNA materials in their pursuit of diagnostics, genetic sequencing, and drug discovery. The basic chemistry for the efficient synthesis of DNA, its modification, its labeling with ligands and chromophores, and its covalent linkage to solid supports are now well developed technologies. Synthetic DNA represents the preferred material into which so many important structural, functional, and mechanistic properties can be combined.

DNA polymers have three important advantages over any of the present polymeric materials used for electronic, and photonic applications. First, DNA polymers provide a way to encode highly specific binding-site identities o semiconductor or photonic surfaces. These sites, produced at defined locations, could be of microscopic (micron), sub-micron, or even molecular (nanometer) dimension. Second, DNA polymers provide a way to specifically connect any of these locations. The pre-programmed DNA polymers self-organize automatically. Finally, DNA polymers provide the building blocks for nanotechnology; they are self-organizing materials for creating true molecular-level electronic and photonic devices.

The specificity of DNA is inherent in the hydrogen bonding properties of the base components (Adenine bonds only with Thymine, and Guanine bonds only with Cytosine). These specific base pairing properties of DNA allow complementary sequences of DNA to "hybridize" together to form the double-stranded structure. It is this inherent property which allows DNA polymers to be used to form programmable self-assembling structures. Thus, when a photonic device has one specific DNA polymer sequence attached to it, it will only bind (hybridize) to a device or surface coated with the complementary DNA polymer sequence. Since a large variety of DNA sequences can be used, multiple devices, each attached to a different DNA sequence can in principle be self-assembled simultaneously. The following lists the important advantages of using DNA polymers for self-assembling nanofabrication applications:

1. DNA polymers can by synthesized both rapidly and efficiently with automated instruments. Conventional polymer chemistries can be significantly more complex and costly to develop.
2. DNA polymers can be synthesized in lengths from 2 to 150 nucleotides, which is the appropriate size range (1 nm to 60 nm) for self-assembling unit cells.
3. DNA polymers can be synthesized with any desired base sequence, therein providing programmable recognition for an almost unlimited number of specific connections.
4. DNA polymers with unique sequences of as few as ten nucleotides are highly specific and will bind only to their complementary sequence. Thus, the material allows specific connections as small as 3.4 nm to be made between molecular units.
5. DNA polymers can be covalently labeled with fluorophores, chromophores, affinity labels, metal chelates, chemically reactive functional groups and enzymes. This allows important photonic and electronic properties to be directly incorporated into the DNA polymers.

6. DNA polymers can be modified at any position in their sequence, and at several places within the individual nucleotide unit. This provides a means to position functional groups for maximum performance.
7. DNA polymers can be both covalently and non-covalently linked to solid surfaces: glass, metals, silicon, organic polymers, and bio-polymers. These attachment chemistries are both existing and easily developed.
8. The backbone structure of the DNA molecule itself can be highly modified to produce different properties. Thus, there is compatibility with existing semiconductor and photonic substrate materials.
9. Modified DNA polymers can be used to form three-dimensional structures, thus leading to ultra high density secondary storage schemes.
10. DNA polymers can be reversibly assembled and disassembled by cooling and heating, or modified to remain in the assembled state. This is a critical property for self-organizing materials as it allows for more options in the manufacture of resulting systems.
11. The structural and organizational properties of DNA polymers (nucleic acids in general) are well understood and can be easily modeled by simple computer programs. Thus, more complex molecular photonic and electronic devices can be designed.

DETAILED DESCRIPTION OF THE INVENTION

Figure 2:
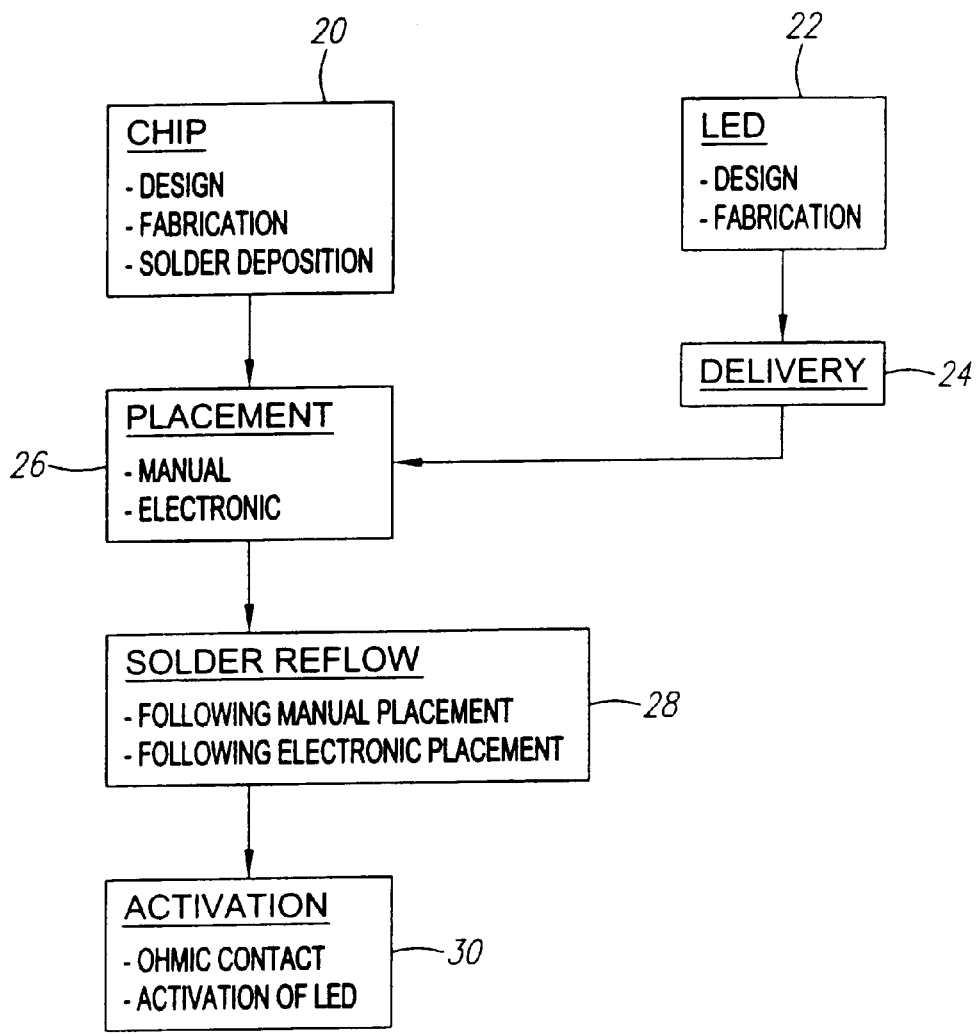
FIG. 2 is a flow diagram of the overall process at one level of generality.
Figure 3:
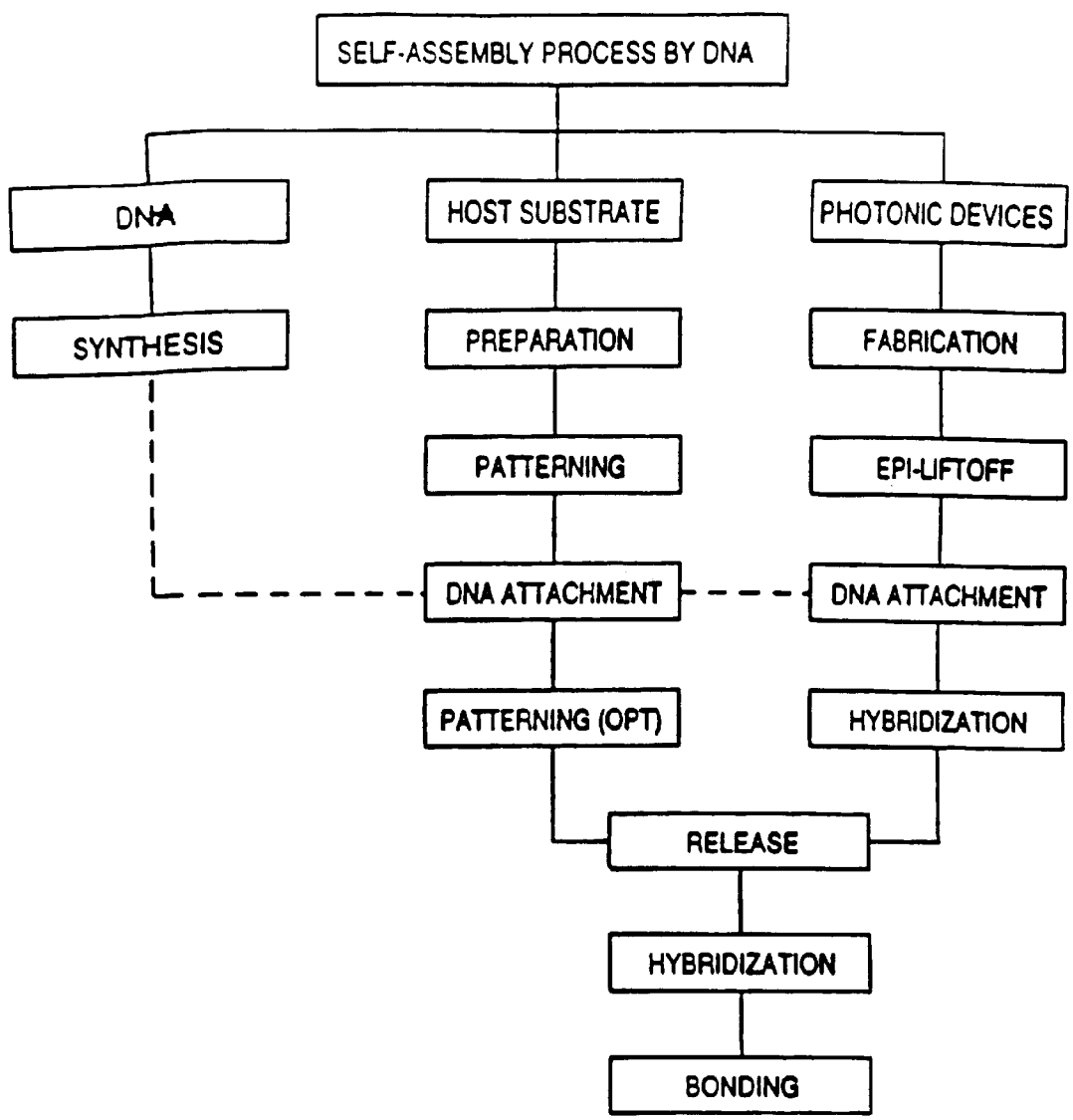
FIG. 3 is a flow diagram of self-assembly processes.

FIG. 2 is a flow chart showing major components typically included in implementation of these inventions. At one level of generality, the inventions utilize the combination of fluidics and electronics for the transport and placement of a component device on a target device (sometimes referred to as a motherboard). Various modes of transport utilizing electronics, typically in a medium, most typically a fluid medium, include electrophoretic transport, electroosmotic transport, and dielectrophoretic action, including orientation and transport. Electrostatic potentials may be utilized with or without the presence of fluid. Electroosmotic transport is typically considered to be surface phenomenon, and accordingly, such transport is typically found close to the surface, most typically a charged surface, which results in a net fluid flow.

FIG. 2 identifies two primary components, a chip or motherboard 20 and a component device 22. Typically, the chip or motherboard 20 will include certain design aspects, described below, which aid in the achieving of the functions of placement, attachment and activation, if required, of the component device 22. Similarly, the component device 22 is designed and fabricated to achieve the requirements of placement, attachment and activation, if required. Typically, the component device 22 is delivered at step 24 to the vicinity of the chip or motherboard 20. The component device 22 may be delivered at step 24 in numerous ways, described below, though in the preferred embodiment, at least a portion of the delivery path includes a fluidic delivery portion. The placement step 26 serves to position the component device 22 in proper relationship to the chip or motherboard 20 to permit the effective attachment and activation, if required, of the component device 22. Attachment step 28 may be achieved by any technique consistent with the other stated goals in functions of the invention, though in the preferred embodiment comprising a solder reflow technique. Namely, solder previously positioned on the chip or motherboard 20, and/or the component device 22 may be made to form a electrical and mechanical attachment of the component device 22 to the chip/motherboard 20. Additional mechanical attachment structures or forces may be utilized as necessary. If required by the nature of the device, activation step 30 serves to permit electronic interaction between the chip or motherboard 20 and component device 22.

FIG. 2 includes certain specifics regarding the placement, attachment and activation of a light emitting diode (LED) as a component device 22. A chip or motherboard 20 may be designed and fabricated such that the LED component device 22 may be attached to it and made active through the operation of the chip or motherboard 20. In one embodiment, the LED component device 22 is of a size (approximately 20 microns in diameter) and weight such that effective electrophoretic placement would not be feasible. Such transport would not be feasible if the charge to mass ratio necessary to effect electrophoretic transport was so high as to cause damage to the component device 22, or could not be achieved through placement of charge on the component device 22. In such a case, electroosmotic flow may be utilized, either alone or in combination with other forces (fluidic, electrostatic, electrophoretic and/or dielectrophoretic) in order to move the component device 22 relative to the chip or motherboard 20 to achieve the desired placement. One the placement step 26 had been achieved for the LED component device 22 relative to the chip 20, electrical attachment may be achieved, such as in the preferred embodiment by performing a solder reflow step 28. In the case of an LED component device 22, provision of power from the chip or motherboard 20 may result in LED activation.

In certain embodiments, these inventions relate to methodologies, techniques, and devices which utilize self-assembling DNA polymers, modified DNA polymers, DNA derivitized structures and other affinity binding moieties for nanofabrication and microfabrication of electronic and photonic mechanisms, devices and systems. This invention also relates to processes which allow multiplex and multi-step fabrication, organization or assembly of modified DNA polymers, DNA derivitized structures, and other types of affinity or charged structures into more complex structures on or within silicon or other surfaces. For purposes of this invention "DNA polymers" is broadly defined as polymeric or oligomeric forms (linear or three-dimensional) of nucleic acids including: deoxyribonucleic acid, ribonucleic acids (synthetic or natural); peptide nucleic acids (PNA); methyphosphonates; and other forms of DNA in which the backbone structure has been modified to produce negative, positive or neutral species, or linkages other than the natural phosphate ester. Also included are forms of DNA in which the sugar or base moieties have been modified or substituted, and polymeric forms of DNA in which nucleotide or polynucleotide units are interspersed with other units including but not limited to phosphate ester spacer moieties, amino acids, peptides, polysaccharides, synthetic organic polymers, silicon or inorganic polymers, conductive polymers, chromophoric polymers and nanoparticles or nanostructures.

For purposes of this invention "electroosmotic" is broadly defined as an aspect of electrophoresis where the electric field causes the relative motion of water molecules and other entities to occur at or near a charged surface.

For purposes of this invention "electrophoretic" is broadly defined as a process for transporting electrically charged entities in solution using an electric field.

For purposes of this invention "dielectrophoretic" is broadly defined as a process involving high frequency AC electric fields which causes the relative movement of molecules or other entities in solution.

For purposes of this invention "electrostatic" is broadly defined as the net electric charge (positive or negative) on a molecule or other entity.

For purposes of this invention "Modified or Derivitized DNA polymers" are broadly defined as nucleic acids which have been functionalized with chemical or biological moieties (e.g., amines, thiols, aldehydes, carboxyl groups, active esters, biotin and haptens) which allow the DNA to be attached covalently or non-covalently to other molecules, structures, or materials. Also included are forms of DNA which have been modified or Derivitized with chromophores, fluorophores, chelates, metal ions, amino acids, peptides, proteins, enzymes, antibodies, or aliphatic or aromatic moieties which change solubility, and moieties which change the net charge on the DNA molecule.

For purposes of this invention "DNA Derivitized structures" are broadly defined as nanostructures (organic, inorganic, biological); nanoparticles (gold, silica, and other inorganic materials); organic or polymeric nanobeads; sub-micron devices, components, particles, (silicon based devices produced by photolithography or E-beam lithography); and micron scale devices or particles which have been functionalized with a specific DNA sequence which allows the structure to be specifically attached or interconnected to another structure, device, or to a specific location on a surface.

While the terms "nanostructure" refers to sub-micron sized structures, terms such as "nano" or "micro" are not intended to be limited in the sense that a micron scale device can be functionalized with DNA polymers which technically have lengths of 10–180 nanometers.

The unique properties of DNA provides a programmable recognition code (via the DNA base sequence) which can be used for specific placement and alignment of sub-micron and nanoscale structures. The basic chemistry and technology required to attach specific DNA sequences to organic, semiconductor, and metallic compounds is known to the art and specific chemistries are described for carrying out such applications.

This fabrication technique has major applications in the field of optoelectronics and in the manufacturing of various hybrid-integrated components including flat panel displays, medical diagnostic equipment and data storage systems. Novel devices with very small physical dimensions take advantage of various quantum confinement techniques. In most cases, these devices are preferably distributed over large areas (e.g. smart pixels and displays). Other devices may be brought together in dense regular crystal lattices (e.g. photonic bandgap crystals). In both cases, the physics of the devices are now understood, and viable fabrication techniques of these inventions are required. With regard to new processing techniques, DNA self-assembly technology allows these devices to be constructed.

Integrated photonic and electronic systems utilize the inventive fabrication technologies including nanostructure fabrication, integration, interconnection and self-assembly techniques. For such applications, DNA self-assembly fabrication technology involves the following steps. Synthetic DNA polymers are designed with highly specific binding affinities. When covalently attached to nanoscale organic, metallic or semiconductor component devices, DNA polymers provide a self-assembly fabrication mechanism. This mechanism can be used for both the selective grafting of devices to specific pre-programmed locations on a desired surface, and for the clustering of devices into pre-programmed 2 and 3 dimensional lattices.

For grafting an array of photonic component devices onto a host substrates, DNA polymers with complementary sequences are first synthesized as shown in FIG. 2. The photonic component devices and desired areas of the host substrate (receptor areas) are coated with the complementary DNA sequences. The host substrate is then introduced into a hybridization solution. The devices coated with the specific DNA polymers are also released from their mother substrate into the solution. The released devices can be actively transported to their receptor areas under the influence of electrically or optically induced local fields (electrophoresis). Hybridization is carried out by carefully controlling the solution temperature, ionic strength, or the electric field strength. Once the devices are grafted via hybridization to their specific receptor areas, the solution is removed and the substrate is dried. Metallurgical (or eutectic) bonding can now be carried out at a higher temperature to fully bond the devices to the host substrate material. The clustering of sub-micron and nanoscale elements into 2-D or 3-D structures (e.g., photonic band-gap crystals), can be carried out in a similar fashion. In this case, the host substrate is replaced by other nanoscale elements. A major difference however, is the attachment technique used to position different DNA strands on the nanoscale elements.

Figure 4B:
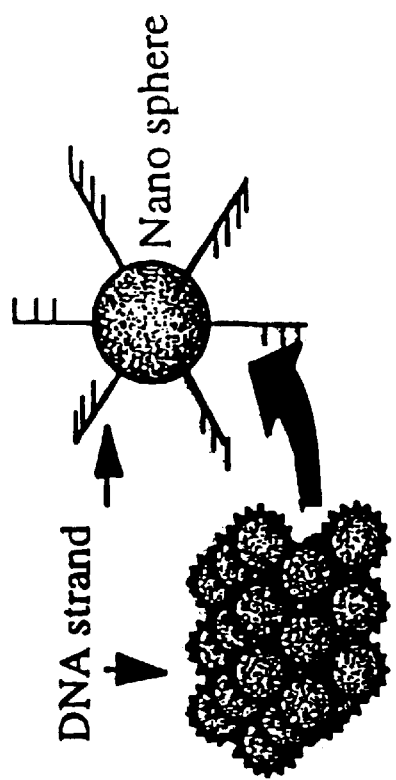
FIG. 4B is a perspective view of a clustering of nanospheres by DNA assisted self-assembly to form synthetic photonic crystals.
Figure 4A:
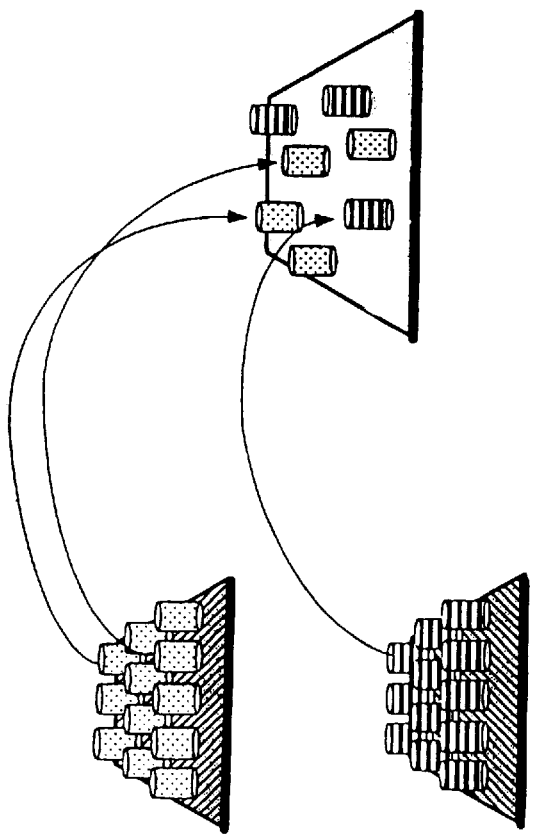
FIG. 4A is a perspective drawing of the apparatus and method for redistribution of photonic devices fabricated as dense arrays onto the host substrate without mother substrate layout constraints.

The self-assembly fabrication technique based on DNA polymers offers two unique features. First, by removing the requirement for conservation of relative device spacing (as defined by the mother substrate) during the device grafting (hybridization) process, the technique enables the micron, sub-micron or nanoscale devices to be fabricated densely on their mother substrates and then be redistributed in a pre-programmed fashion onto the host substrate (FIG. 4A).

This feature has a profound impact on the viability of intra-chip optical interconnects within large chips. It lowers the cost of silicon based smart pixels where photonic devices must be fabricated on more expensive smaller substrates. The second feature is the ability to manipulate and orient with respect to each other a large number of nanoscale devices (e.g. organic or metallic nanospheres). This feature allows the "growth" of synthetic photonic crystals with large lattice constants possessing desired orientation symmetries for exhibiting photonic bandgap properties (FIG. 4B).

Thus, the highly specific binding affinities and self-assembly of DNA polymers can lead to:

(1) Low cost smart pixels and display devices by enabling photonic or electronic micron or nanoscale devices to be self-assembled and integrated over very large areas of silicon or other substrates, i.e. the self-assembly of an arrays of light emitters on a silicon substrate, (2) Highly selective wavelength and tunable devices by enabling dielectric nanostructures to be self-assembled to form photonic bandgap crystals, i.e. the encapsulation of emitter devices within a photonic bandgap crystal layer created by the self-assembly of DNA nanospheres, (3) Ultra high density optical storage media by enabling chromophore molecules and nanostructure units to be selectively self-positioned, and (4) The selective positioning of bonding structures, such as gold, tin or solder structures as bonding pads, e.g., to achieve low cost or unassisted die-to-die processing, e.g., for flip-chip applications.

In the preferred embodiment, these applications require four steps in the process. The first involves the design and synthesis of the DNA polymer sequences and their selective attachment to the sub-micron and nanoscale devices of interest. Second, attachment of specific complementary DNA polymers to pre-selected receptor locations on a host substrate surface. Third, the self-assembly of the devices by the DNA hybridization process. The fourth process involves establishing the electrical contacts.

This invention brings together molecular biological (DNA structure and function) and photonic and electronic device principles in a synergistic manner. On the photonic device side, novel devices with very small physical dimensions take advantage of various quantum confinement techniques. In most cases, these devices must be distributed over large areas (e.g. smart pixels and displays). In other cases, these devices must be brought together densely to form regular crystal lattices (e.g. photonic bandgap crystals). With regard to processing techniques, self-assembly DNA techniques with its well developed base of DNA synthesis, modification, and hybridization is an enabling technology for these applications. DNA linkage to solid supports and various other materials is possible via a variety of processes for attaching DNA selectively to silicon, gold, aluminum and other inorganic and organic materials. A number of thin film processing techniques are highly complementary with these DNA processes. For example, as will be described later, the lift-off process can be easily adapted to produce micron, and sub-micron devices with attached DNA sequences.

Experimental-Transport of Led As Component Device to A Motherboard

Figure 5:
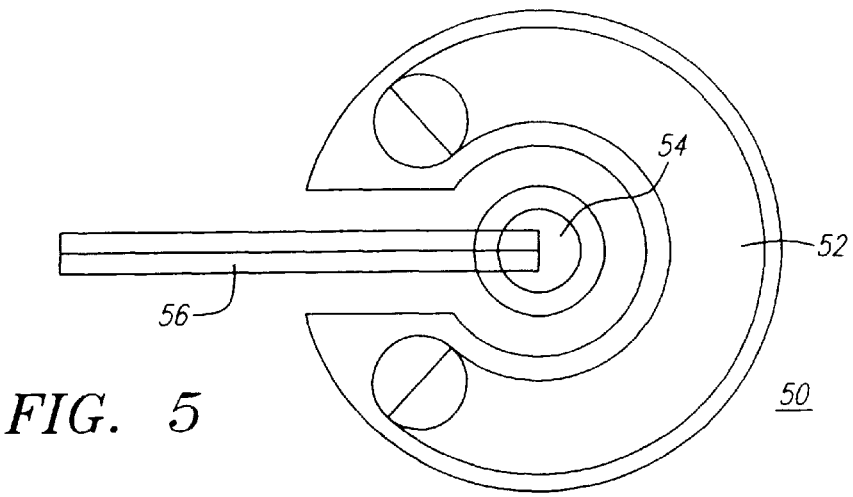
FIG. 5 is a plan view of the contact and lead portions of the target substrate or motherboard.
Figure 6:
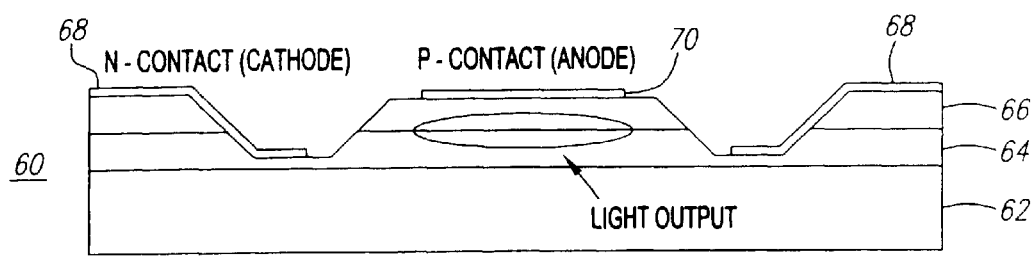
FIG. 6 is a cross-sectional view of a light emitting diode (LED) adapted to be transported through a fluidic medium to the target shown in FIG. 5.

A light emitting diode (LED) has been transported and placed principally through electroosmotic force onto a target portion of a chip or motherboard, electrically connected and mechanically attached thereto, and activated. FIG. 5 is a plan view of the contacts and structures on the chip or motherboard. FIG. 6 is a cross-sectional drawing of a component device LED adapted to be placed, attached, and activated through the contact structure of FIG. 5.

FIG. 5 shows a generally planar structure having a first electrode 52, second electrode 54 and lead 56 disposed on the surface or substrate 50 of the chip or motherboard. The first electrode 52 is shown having a horseshoe shape, being an annularly shaped electrode being substantially continuous throughout the electrode region, and having two terminal ends. The second electrode 54 may also be termed a center electrode or contact or anode contact. As shown, the center contact 54 is directly and electrically connected to lead 56. Lead 56 is disposed between, but spaced apart from, the terminal ends of the first electrode 52.

FIG. 6 shows one implementation of a light emitting diode/component structure 60. A substrate 62 includes a first layer 64 disposed thereon, and a second layer 66 in contact with the first layer 64. The interface between the first layer 64 and second layer 66 serve to generate light from the LED 60. The light is generally emitted from the LED 60 in a downward direction as shown in FIG. 6 through the substrate 62. A first electrode 68 is disposed on the device 60 so as to contact the second layer 66 and first layer 64. The first electrode 68 is generally annular in shape and forms a continuous ring or band around the device 60. The second electrode 70 is disposed on the outward facing portion of the second layer 66. Generally, the second electrode 70 is of a circular disk-like shape. The second electrode 70 comprises the anode contact for the P-region which constitutes the second layer 66. The first electrode 68 serves as the electrical contact for the first layer 64 which constitutes the end-region.

When placed in an assembled condition, the LED of FIG. 6 is positioned such that the first electrode 68 in its annular portion disposed on the outward facing surface of the second layer 66 is in contact with the first electrode 52 of FIG. 5. The second electrode 70 contacts the center contact 54 on the substrate 50.

Figure 7:
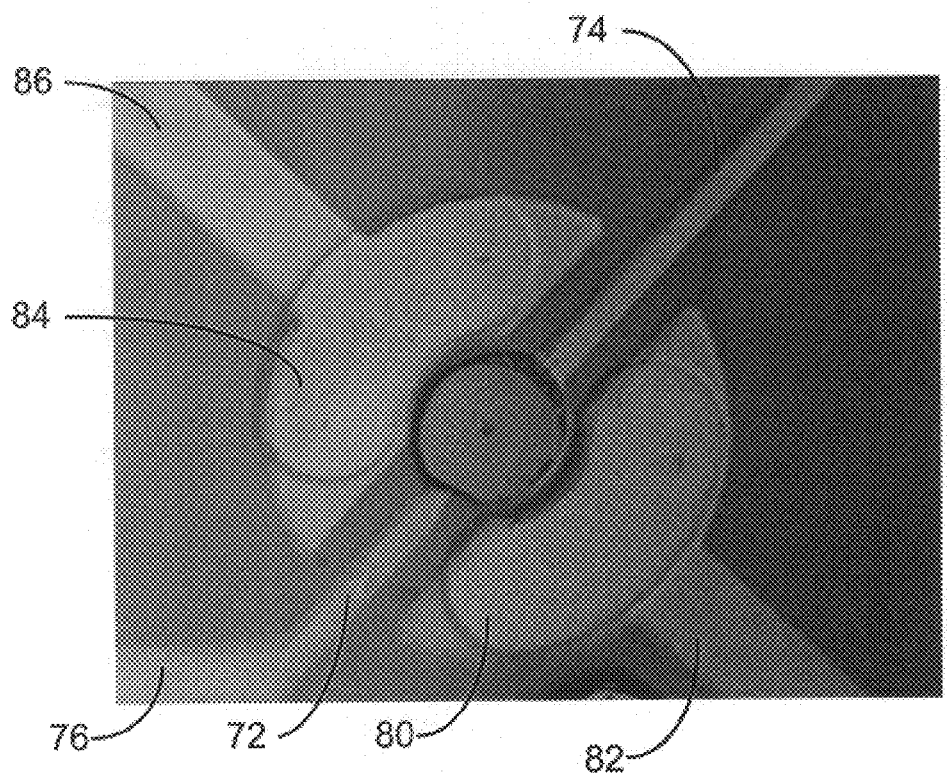
FIG. 7 is a plan view of a LED positioned adjacent locating electrodes.

FIG. 7 shows a microphotograph in plan view of a target site and LED. The LED 72 is disposed above, and obscures, a center contact 54 and horseshoe shaped cathode 52 (previously described in connection with FIG. 5). Lead 74 connects directly to the center contact 54 and lead 76 electrically contacts the center contact 54 and lead 76 electrically contacts the center contact. A first drive electrode 80 is disposed proximal to the target location for the LED 72. A second drive electrode 84 is disposed in a mirror image relative to the transported device, that is, the LED 72. The drive electrodes 80, 84 are contacted with a first drive electrode lead 82 and a second drive electrode lead 86, respectively. The leads 82, 86 serve to provide electrical contact to the drive electrodes 80, 84 from a power supply and control system. As shown in FIG. 7, each of the drive electrodes 80, 84 is quasi-kidney shaped. Alternate shapes consistent with the functionality of transport, placement and/or attachment may be utilized. For example, sections of an annular ring may be utilized.

FIG. 8 is a cross-sectional, diagrammatic view of an advantageous technique for the placement or positioning of a movable component device 90. A host device or motherboard 92 includes a surface 94. In operation, the surface 94 is generally disposed in an upward oriented configuration, and is adapted to receive the movable component device 90. Ordinarily, the surface 94 is horizontally disposed, such that the movable component device 90 is subject to no or minimal lateral gravitational forces. In that way, the controllable electrical forces, e.g., electroosmotic force, serves to place the movable component device 90 in the desired location. The surface 94 receives the solution, typically a buffer solution, in which the movable component device 90 is placed.

Figure 8A:
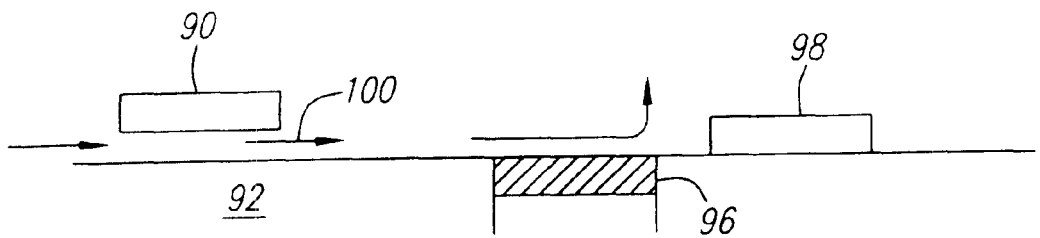
FIGS. 8A, 8B and 8C show a motherboard and associated device for placement and attachment, including fluidic flow paths, FIGS. 8A and 8B showing flow paths from a drive electrode and FIG. 8C showing the flow path for the center electrode.
Figure 8B:
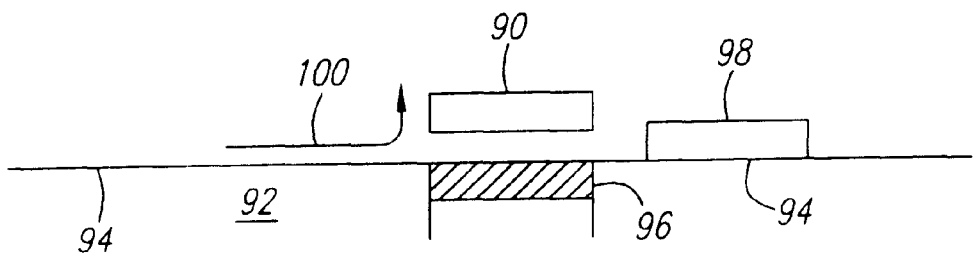
Figure 8C:
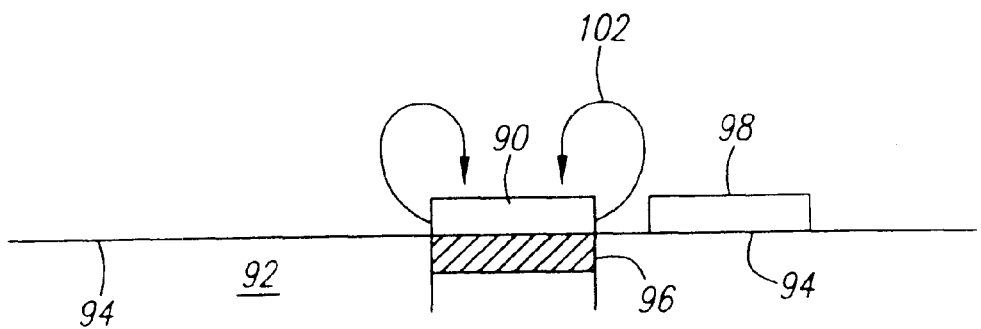
Figure 9:
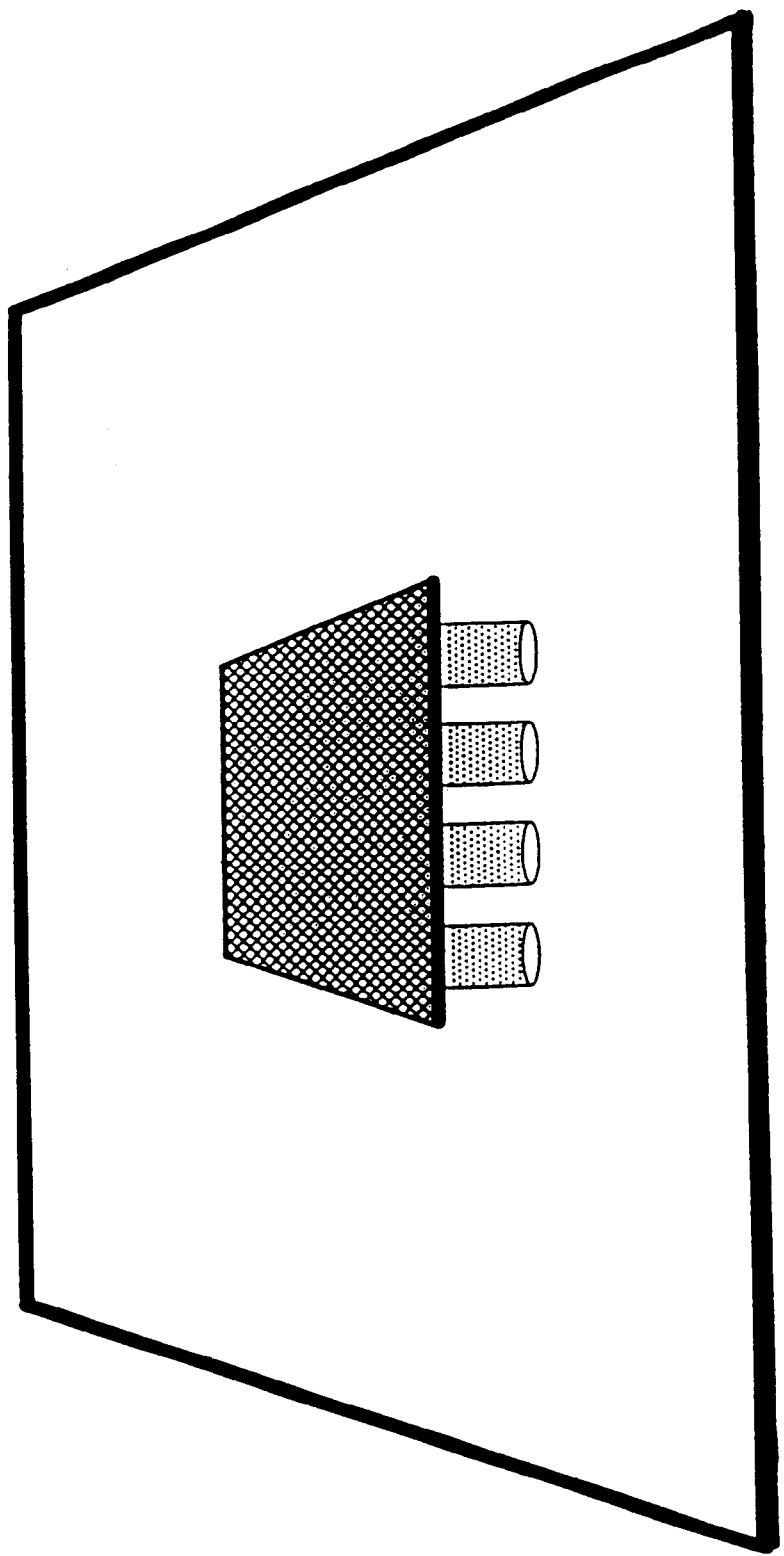
FIG. 9 is a perspective view of a flip-chip bonding arrangement which conserves the geometrical dimensions leading to the coupling of small dense arrays of specialty devices onto local regions of mother boards.

FIG. 8 shows one advantageous mode of operation of a motherboard in order to place a movable component device 90 at a desired electrode location 96. FIG. 8A shows the movable component device 90 disposed above the surface 94 of the substrate 92. The electroosmotic flow current 100 is shown moving in a generally rightward direction on the surface 94 of the substrate 92. A drive electrode 98 is the active electrode for the creation of the electroosmotic current and flow 100. The movable component device 90 is subject to a lateral force in a rightward direction, causing its motion toward the target location, namely, the electrode location 96. The electroosmotic flow 100 as it reaches the drive electrode 98 is in a generally upward direction. As shown in FIG. 8B, the movable component device 90 has been moved into location above the electrode 96. The electroosmotic flow 100 path may then be altered slightly based upon the physical presence of the movable component device 90. The movable component device 90 may be approximately positioned above the electrode 96 via the drive electrode 98. FIG. 8C shows an advantageous technique for the placement of the movable component device 90 more precisely on the electrode location 96. By deactivating the drive electrode 98, and activating the electrode location 96 so as to cause electroosmotic flow in the general flow current 102, the movable component device can be caused to be affirmatively pressed to the electrode 96 through the action of the electroosmotic flow and pressure generated therefrom. In this manner, the gross or rough positioning or placement of the movable component device 90 through action of the drive electrode 98 may be achieved, followed by the precise positioning of the movable component device 90 achieved through action of the electrode location 96.

Detailed Procedures For LED Placement and Attachment

Pretreatment

The electrode array chips undergo a $O_2$ plasma cleaning followed by a Ar plasma cleaning step (10 min each). The chips are then placed in a medium sized plastic petri dish containing two droplets of water and about 100 $\mu l$ of (Heptadecafluoro-1,1,2,2-tetrahydrodecyl) dimethylchlorosilane (Gelest). The petri dish is partially covered and evacuated (house vacuum) for about 15 min. The chips are placed in a clean glass petri dish and cured at 90 C. for 15–30 min.

Plating

The active electrode area is determined for each chip by running a cyclic voltamogramm (CV) in an aqueous solution of 0.1 M. $K_2K_3Fe(CN)_6$ and 0.5 M KCl and comparing with the CV obtained from a 80 $\mu m$ circular electrode. The determined area is then used to calculate the necessary current corresponding to 3.75 $\mu A$ on a 80 $\mu m$ circular electrode. The chip surface is thoroughly rinsed with water and then covered with tin-lead (40:60) electroplating solution (Techni Solder Matte NF 820 HS, Technic Inc.) A constant current is applied for several seconds to produce the desired plating height. The plating solution is immediately removed and replaced by a 0.1M pH 5.2 sodium acetate buffer solution. Vigorous stirring is necessary to dissolve any precipitates. The chips is thoroughly rinsed with water and air dried.

LED Lift-Off

Standard procedure

The GaAs substrate is removed from the attached Si wafer by heating above 100 C. to melt the wax that is used for attachment. The freed GaAs wafer is then soaked in dichloromethane for 15–45 min (to remove the wax), followed by a rinse with isopropanol and water. After drying the wafer is immersed in buffered HF (6:1) for 150 sec and then soaked in water. After drying the wafer is immersed in conc. HCl for 60 sec and then soaked in water. At this point usually a majority of the LEDs can be removed from their sockets with a micromanipulator tip.

Modified procedure

A short exposure (20 sec) to conc. HF/Ethanol 1:3 accomplishes lift-off easily (many LEDs get removed from their sockets) without affecting the LEDs' performance.

Aging

LEDs once lift-off tend to re-adhere strongly to the substrate over time. They can be re-released by short exposure (30 sec) to conc. HCl.

Plasma Cleaning

Plasma cleaning (Ar or $O_2$) has no effect on the lift-off of LEDs. However, it has an impact on the behavior of LEDs in solution. Ar plasma cleaned LEDs adhere strongly to the $SiO_2$ chip surface and can hardly be flipped gold side down. Once flipped they tend to flip back very easily.

LED Derivatization

Thiolacetic Acid/Thiolethylamine

New LEDs are first soaked in acetone followed by isopropanol and water and then air dried. Used LEDs are $O_2$/Ar plasma cleaned (10+10 min). The cleaned LEDs (on their substrate) are immersed in 1–10% solutions of the respective thiol in 1:1 isopropanol/water for 60–120 min and then soaked in 1:1 isopropanol/water followed by water.

Silanes

Prior to deposition the LEDs are $O_2$ plasma cleaned (10 min). Volatile silanes are deposited as vapors at ambient or reduced pressure for 15 min. Curing is performed at 90 C. for 15–30 min.

Non-volatile silanes are deposited from 2% solutions in 200 proof ethanol (10 min). After deposition the samples are rinsed with ethanol and cured at 90 C. for 15–30 min.

LED Transfer

Standard Procedure

A water soluble glue is prepared by mixing 5–6 g of Ficol 400 into 2.5 ml glycol and 0.5 ml water. This mixture is very hygroscopic and relatively quickly changes its consistency. Ideally, the glue should stay at the tip of a fine micromanipulator tip without wicking back by capillary force. LEDs are removed from their sockets with a clean probe tip. The very tip of the probe is brought in contact with the glue. A minimal amount of glue is used to pick-up and transfer the LED. The probe tip with the LED is moved to the surface of a dry chip. Water is added to the chip and the LED is released from the probe tip due to dissolution of the glue. The probe tip is removed and cleaned. The chip is rinsed 2× with water, soaked for 1 min and then rinsed once more (Eppendorf pipette). After removal of the water, 10 mM aminocaproic acid solution is added to the chip. If the LED is oriented the wrong way, it can be flipped either by introducing turbulence with a probe tip or by moving the LED close to an electrode followed by application of a short pulse of current (100–200 nA).

LED Movement and Alignment

LEDs that are oriented with their gold contacts facing upwards tend to stick to the surface and do not move. If the gold contacts are facing towards the substrate surface the LEDs tend to hover and can be easily moved (electronically, by probe tip movement or by convection).

In 10 mM $\epsilon$-aminocaproic acid currents of about 100–300 nA are sufficient to move an LED across several hundred microns.

Standard Procedure:

A cathodic current (100–300 nA) is applied to one of the two drive electrodes (the one that is more distant from the LED) using the ring electrodes as counter electrodes. As soon as the LED starts accelerating towards the electrodes, the current is continuously adjusted to maintain a steady movement. (If the movement is too slow the LEDs can get stuck to the surface. If the movement is too fast the LEDs can get flipped in vicinity of the electrodes.) Once the LED is close to the space between the two drive electrodes, the second drive electrode is activated without increasing the current. At this point current levels of about 10–30 nA should be sufficient to keep the LED close to the contact electrodes. By varying the current at low levels (5–15 nA) the LED is centered above the contact electrodes. Once the LED is centered, the outer contact electrode is activated as counter electrode while the ring electrodes are disconnected. The current (2–15 nA) now flowing between the drive electrodes and the outer contact electrode forces the LED down onto the surface. If the LED is not sufficiently centered the previous step is reverted and then repeated. Immediately after this step the liquid is removed and the electrodes disconnected (over time larger currents are needed to keep the LED positioned).

Contact Formation

Standard procedure

The LED/substrate assembly is air dried and then exposed to an Ar plasma (ca. 250 W at 250 mTorr) for 10 min. This process physically attaches the LED to the contact electrodes. A few microliters of flux (Alphametals 2491–121) are applied to the surface. The sample is enclosed in a reflow chamber that is purged with a gentle flow of forming gas (95% $N_2$, 5% $H_2$). The flux solvent is dried off at 60 C. until the solid flux components precipitate. The sample is then heated at a rate of about 90 C./min to a final temperature of 250 C. The heater is turned off and the forming gas flow is increased to let the sample cool down.

Electric Field Assisted Assembly Under Low Gravity Conditions

One aspect of this invention concerns the potential to improve the performance of electric field assisted pick and place processes for heterogeneous integration under low gravity conditions. Low gravity conditions would allow the pick the electric field assisted processes to be carried out under overall lower field conditions than under normal gravity. Thus, larger and heavier micron-scale objects could now be transported, orientated, and positioned much more effectively then under normal gravity conditions. Thus, the electric field assisted processes may prove more useful and viable when carried out in space platforms (space stations) were low gravity conditions exist. In another aspect of this invention electric field assisted assembly under low gravity conditions may be carried out without the need for a fluidic environment, by using controlled electric fields to transport and manipulate objects which have an electrostatic charge.

Key Process for DNA Based Component Device Self-Assembly

Four techniques are important for the DNA based component device self-assembly process. These are the DNA polymer synthesis, DNA attachment chemistry, DNA selective hybridization and epitaxial lift-off of semiconductor thin films and devices. In the following sections we provide brief summaries of these techniques.

DNA Synthesis and Derivatization

The synthesis of the DNA polymer or oligomer sequences, their purification, and their derivatization with the appropriate attachment and chromophore groups can be carried out in the following preferred manner: DNA sequences are synthesized using automated DNA synthesizer and phosphoramidite chemistry procedures and reagents, using well known procedures. DNA polymers (polynucleotide, oligonucleotides, oligomers) can have primary amine groups incorporated at chemical bonding sites for subsequent attachment or functionalization reactions. These primary amine groups can be incorporated at precise locations on the DNA structure, according to the need for that particular sequence. Attachment sequences can also contain a terminal ribonucleotide group for subsequent surface coupling reactions. Sequences, including the amino modified oligomers, can be purified by preparative gel electrophoresis (PAGE) or high pressure liquid chromatography (HPLC). Attachment sequences with terminal amino groups can be designed for covalent bonding to gold, silver, or aluminum metalized features or to small areas where silicon dioxide is present. These sequences can be further Derivitized with a thiolation reagent called succinimidyl 3-(2-pyridyldithio)propionate (SPDP). This particular reagent produces a sequence with a terminal sulfhydryl group which can be used for subsequent attachment to metal surfaces. Other attachment sequences containing a terminal ribonucleotide group can be converted to a dialdehyde derivative via Schiff s base reaction. These attachment sequences can then be coupled to aminopropylated silicon dioxide surfaces. Specific sequences designed for electronic or photonic transfer responses can be functionalized with their appropriate chromophore, fluorophore, or charge transfer groups. Many of these groups are available off-the-shelf as activated reagents that readily couple with the chemical bonding sites described above to form stable derivatives.

DNA Attachment to Solid Supports and Preparation of the Host Substrate Materials This step involves the covalent coupling of the attachment sequences to solid support materials. In the general area of DNA attachment to solid materials, sequences have been covalently attached to a number of materials which include: (i) Glass ($SiO_2$), (ii) Silicon (Si), (iii) Metals (Gold, Silver, Aluminum), and (iv) Langmuir-Blodgett (LB) films. Glass, silicon, and aluminum structures have been prepared in the following manner. Glass and silicon ($SiO_2$) are first treated with dilute sodium hydroxide solution and aluminum with dilute hydrogen fluoride solution. The materials are then Derivitized for covalent coupling with the attachment sequences by treatment with 3-aminopropyltriethoxysilane (APS). This is carried out by refluxing the materials for 2–5 minutes in a 10% APS/toluene solution. After treatment with APS, the materials are washed once with toluene, then methanol, and finally dried for 1 hour at 100° C. Attachment to the APS Derivitized materials is carried out by reaction with the specific dialdehyde Derivitized attachment oligomer (see FIG. 4) for 1–2 hours in 0.1 M sodium phosphate buffer (pH 7.5). In addition, attachment to metal (gold, silver, aluminum) and organic features can be carried out.

To delineate the areas where the grafting of the specialty devices will take place, a selective attachment procedure for the complementary DNA polymer may be carried out. The selective attachment can be realized by using the inherent selectivity of DNA sequences, selective attachment chemistries, or by directed electrophoretic transport. Alternatively after attachment, the DNA strands in unwanted regions can be destroyed by UV radiation. This approach is useful only when one group of devices need to be self-assembled. This approach would in normal operation preclude subsequent DNA attachment processes, and would not allow for the self-assembly of several specialty device groups. Attachment chemistry is strongly dependent upon the materials used to which the DNA polymers may be attached.

For example, to attach DNA to aluminum pads on a silicon chip coated with a protective glass layer, the aluminum regions are activated by dipping the sample for a short period of time into a dilute buffered HF solution. The end result of this process is that only a few DNA strands are attached to the protective glass layer while the exposed aluminum pads are highly reactive to DNA. This material selectivity is a convenient and general way to attach DNA to the desired regions. When material selectivity is combined with UV directed inactivation and electrophoretic transport, this allows for repeatable attachment processes to be carried out sequentially.

Consider the simultaneous self-assembly of several types of specialty devices. The receptor pads need to be grouped according to the device to which they are to be coupled. In this case, each pad group needs to be coated with a specific DNA sequence complementary to the DNA sequence attached to the specialty device that it would be bonded to. In order to "pre-program" the receptor pads, each DNA sequence is attached sequentially to the proper pads. This can be easily achieved by using the electrophoretic transport process and by applying a negative potential to the pads where DNA attachment is not desired. Simultaneously, a positive voltage can be applied to enhance attachment to the desired locations. Alternatively, an optically induced electric field can be used to migrate the DNA strands to desired locations. For a second set of DNA sequence attachment, the procedure is repeated. It should be pointed out that when only one type of device needs to be self-assembled on the host substrate, the use of the material selectivity of the DNA attachment chemistry alone is sufficient. UV radiation of the regions where DNA hybridization is not desired, would be carried out.

Component Device Preparation and Epitaxial Lift-Off

Another key step for the self-assembly process is the preparation of the sub-micron and micron-scale component devices for DNA attachment, their handling during the attachment process, and their final release into solution prior to hybridization. The epitaxial lift-off (ELO) process can substantially improve these aspects of this technique. Epitaxial films in the thickness range of 20 nm to 10 mm have been separated from their growth substrates, handled and manipulated. For example, using this technique thin III-V semiconductor films have been direct-bonded to foreign substrates, such as processed silicon wafers. Prior to lift-off, various devices can be fabricated on the films while still on their mother substrates. The first step in our self-assembly technique is the preparation of the photonic devices that are to be grafted. FIG. 5 describes a preferred process flow for this preparation step. The photonic devices are fabricated in a standard fashion on their mother substrates on a sacrificial layer as required by the ELO process. A suitable coating layer is then deposited on these devices. By controlling the characteristics of the deposited material with respect to device materials the behavior of the devices once released into the saline solution can be controlled. For example, by controlling the coating material properties the direction of the devices in the solution can be controlled. A thick polyamide film is spun to provide a physical support to the devices after the ELO process. The ELO process is carried out and the thin film devices are separated from their mother substrates. By using plasma etching, the polyamide holding membrane is recessed in areas with no devices. If needed, a metal layer can be deposited to assure good electrical contacts to the photonic devices. The DNA attachment process is then carried out and a specific DNA sequence is covalently attached on all metal surfaces. By irradiating the front surface with a UV light, the photonic devices are used as a self-aligned mask enabling exposure of polyamide areas coated with DNA polymer. In these areas, the DNA polymers react to a form that is not suitable for further hybridization. By using a solvent, the polyamide may then be removed and the devices released into the saline solution used for the further hybridization processes.

Selective DNA Hybridization Techniques

Once the host substrate is pre-programmed and the component devices are released into the solution, the self-assembly process can take place. Two different approaches for hybridization are applicable: (1) Conventional hybridization and (2) Active hybridization using an electric field.

For the conventional hybridization process, all devices may be released simultaneously into the solution. By gently agitating the devices in the solution at the proper hybridization stringency temperature and ionic strength, hybridization of the complementary DNA strands takes place as the proper device-receptor pairs come into contact. The probability of hybridization taking place may be related directly to the probability of the proper device-host pad pairs coming into contact. Since the probability distribution is most likely random, this process may take longer to achieve reasonable hybridization yields on large area surfaces unless the solution is saturated with the devices. In order to improve the selectivity and alignment accuracy several controlled heating and cooling cycles may be carried out during the hybridization process. During the heat cycle, weakly hybridized components are dissociated away to increase the chances of forming stronger bonds.

For active or electronic hybridization, the motherboard itself or another electrode array manufacturing device are used to produce localized electric fields which attract and concentrate selected component devices at selected locations. For this process the motherboard or manufacturing device has sites which can be used as an electrodes. A potential is applied across the solution between selected receptor sites and auxiliary electrodes. Receptor sites biased opposite (+) to the net charge (−) on selected devices, now affect the electrophoretic transport and concentration of these devices thereby increasing the rate of hybridization and binding. These sites can be selectively switched on or off using electronic or photonic addressing. A pulsing DC or biased AC electric field can be applied at a suitable frequency to eliminate the screening effect of the unwanted device types.

The electric field effect can also be used in a protective manner. In this case, the receptor pads are now biased the same (−) as the net charge (−) on the devices. The devices are then repelled from these regions and interact or bind only to those locations which have the opposite charge (+) or are neutral. Active electric field transport can be used to carry out multiplex and multi-step addressing of component devices and structures to any location on the motherboard array.

Another important consideration during hybridization is the alignment accuracy of the photonic devices on the motherboard or host substrate. It is assumed cylindrical photonic devices that rotation is invariant. In this case, if the device and host pad diameter is d, an alignment accuracy of d/2 may be first achieved with the natural hybridization process prior to the drying process. Devices that are misaligned with more than d/2 misalignment will not form a strong bond during the hybridization process and will not be held in place during the heating and cooling cycles of the hybridization process. Better alignment accuracy and orientation are possible when active electric field hybridization is used. Once the substrates are removed from the solution, increased surface tension during the drying process could further improve the alignment accuracy.

Metallurgical Bonding

After the hybridization process the specialty devices are held in their proper places through the formation of the double-stranded DNA structure which has a very high bonding strength. The entire assembly is then cleaned by rinsing and then dried. The DNA bond strength remains in the solid state and serves to keep the devices in place. At this point of the process, there is however, no electrical contact between the host substrate and the photonic devices. One method to achieve a metallurgical bond exhibiting an ohmic contact between the host substrate and the photonic devices is to use conductive materials on the pads and devices that can be bonded together eutectically at low temperatures. A second method is to use metals with low melting temperatures like solder or indium under a metal layer that is active for DNA attachment. While the photonic devices are held in place by the DNA bonds, the application of heat will result in the formation of a metallurgical bond. The DNA polymer will disintegrate within the bond but may only contribute to an increased contact resistance depending on the initial DNA loading factor used.

Development of Self-Assembled Emitter Arrays

As one example of the utility of these inventions, emitter arrays can be advantageously formed. Specific DNA polymer sequences may be covalently attached to semiconductor light emitting diodes (LED) and the complementary DNA sequences may be attached to receptor pads on the host silicon substrate. UV/DNA patterning techniques may be used for selective activation/inactivation of DNA on the coated surfaces. All DNA Derivitized test structures and materials will then be tested for selective hybridizability using complementary fluorescent DNA probes. LED test devices Derivitized with specific DNA sequences may be hybridized to test substrates Derivitized with complementary DNA sequences.

Development of Self-Assembled Photonic Band-Gap Structures

Photonic or crystals may be formed using the DNA self-assembly technique. Photonic Bandgap Structures are artificial periodic lattice structures in two- or three-dimensional arrangements and composed of elements of proper dimensions, density and separations. Such structures result in the modification of photonic density of states and a gap in the electromagnetic wave dispersion. Indeed, photonic bandgap structures operating at specific optical wavelengths have been demonstrated. Potential applications of photonic bandgap materials include tailoring of the spontaneous emission of a laser to achieve ultra-low threshold lazing, improved wave guiding structures without radiation loss, novel optical modulators, etc.

The various DNA polymer (oligonucleotide) sequences described above, in the 20-mer to 50-mer size range, may be synthesized on automated DNA synthesizers using phosphoramidite chemistry. Longer DNA sequences are generally required to bind larger objects to surfaces because the binding force must be sufficient to overcome forces (e.g., shearing forces) tending to remove the object. Longer DNA sequences (>50 mers) may be constructed using the polymerize chain reaction (PCR) technique. The DNA sequences may be further Derivitized with appropriate functional groups (amines, thiols, aldehydes, fluorophores, etc.). All sequences may be purified by either PAGE gel electrophoresis or HPLC. After purification, all sequences may be checked on analytical PAGE gels for purity, and then tested for specificity by hybridization analysis.

Several DNA sequences may be used to develop and test additional chemistries for the covalently attachment to various, organic polymer based nanospheres, semiconductor, and other material substrates (glass, gold, indium tin oxide, etc.). Additional attachment chemistries provide more options and flexibility for attachment selectivity to different semi-conductor materials.

Specific DNA polymer sequences may be covalently attached to semi-conductor test structures and the complementary DNA sequences to test substrate (motherboard) materials. UV/DNA patterning techniques may be used for selective activation/inactivation of DNA on the coated surfaces. All DNA Derivitized test structures and materials will then be tested for selective hybridizability using complementary fluorescent DNA probes.

Nanospheres, nanoparticles, and semi-conductor test structures Derivitized with specific DNA sequences will now be hybridized using both conventional (temperature, salt, and chaotropic agents) and electronic (electrophoretic) techniques to the test substrates (motherboards) Derivitized with complementary DNA sequences. The hybridization techniques may be optimized for highest selectivity and least amount of non-specific binding.

Fabrication of an LED Array

Specific DNA polymer sequences may be covalently attached to semi-conductor light emitting diode (LED) component devices and the complementary DNA sequences to motherboard materials. UV/DNA patterning techniques may be used for selective activation/inactivation of DNA on the coated surfaces. LED component devices Derivitized with specific DNA sequences are then hybridized to test substrates (motherboards) Derivitized with complementary DNA sequences.

Self-Assembly Fabrication of a Photonic Crystal Structure

Multiple specific DNA polymer identities may be incorporated into nanoparticles or nanospheres for the self-assembly around emitter test devices located on motherboard materials. UV/DNA patterning techniques may be used for selective activation/inactivation of DNA on the coated surfaces. Nanoparticles Derivitized with specific DNA sequences will now hybridized to the emitter test devices located on the substrates (motherboards) Derivitized with complementary DNA polymers.

Further Aspects Of Self-Assembly

Figure 10:
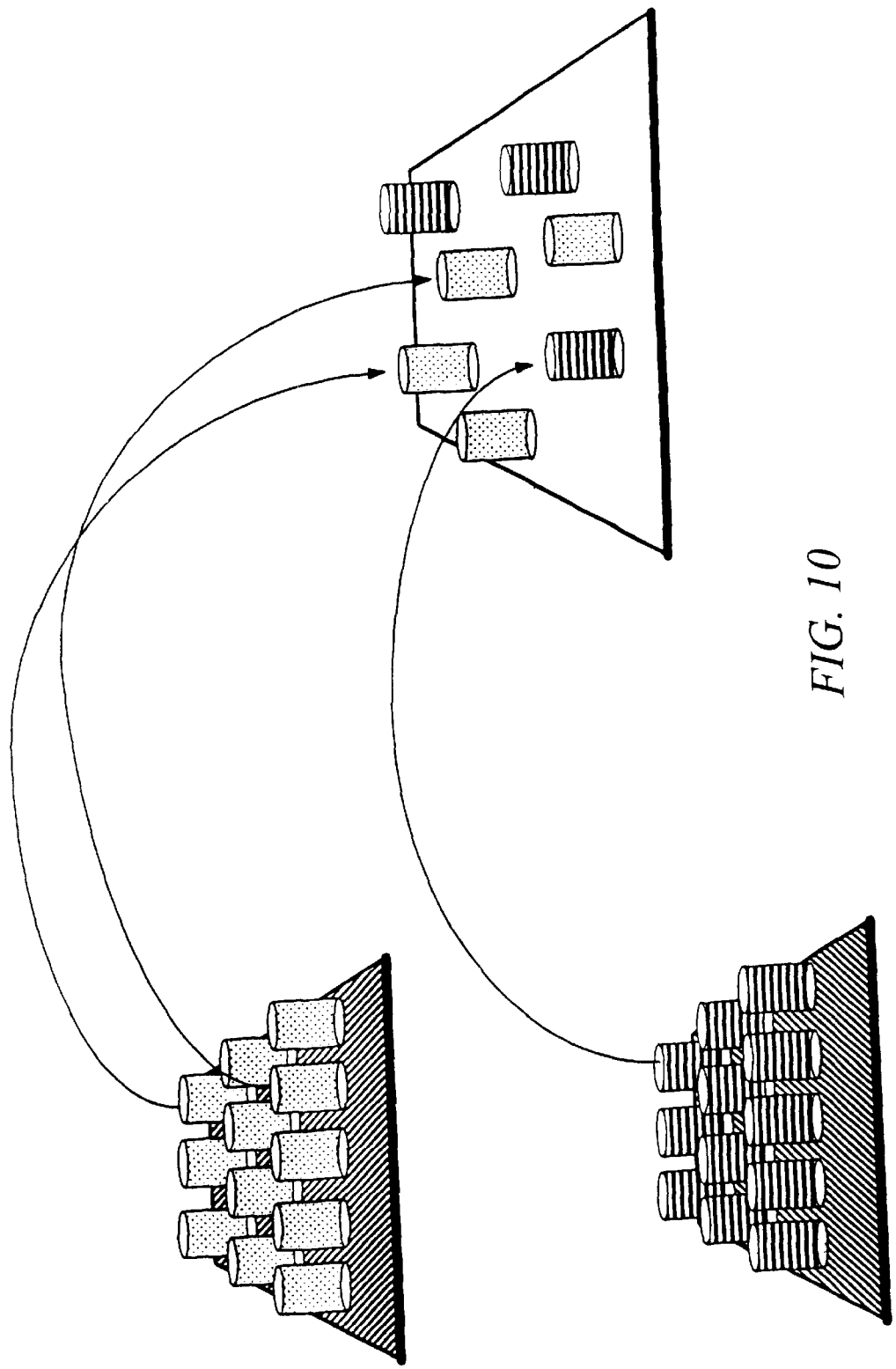
FIG. 10 shows a perspective view of global distribution of small dense structures from small dense chips on to less dense mother boards.
Figure 11:
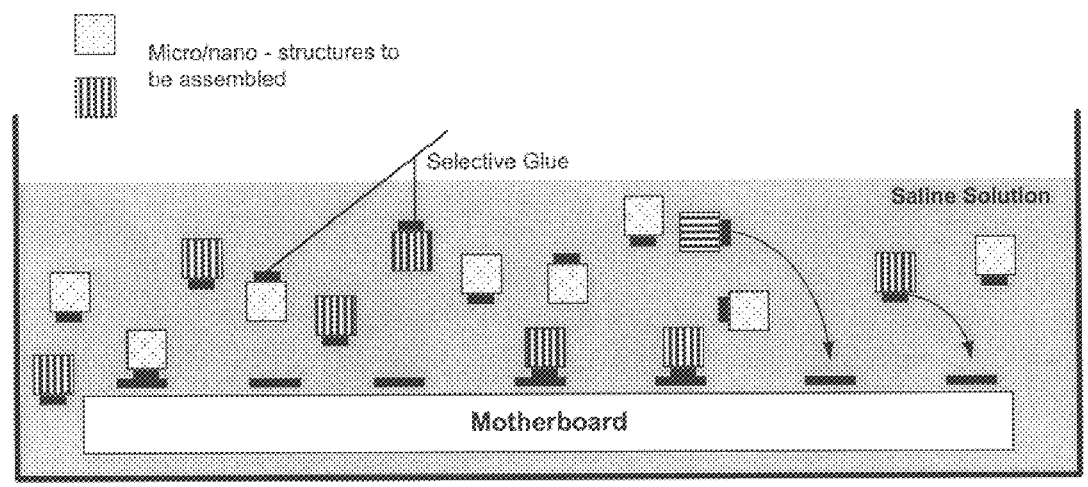
FIG. 11 shows a cross-sectional view of a structure for the self-assembly of micro or nanostructures utilizing a selective glue in which specialty devices of the given type are provided with a specific DNA polymer glue, the areas where these devices must attach being covered with the complimentary DNA glue.

This invention provides for assembling specialty devices in parallel and over larger areas (up to several meters on a side) using a "self-assembly" technique. In this approach, each device to be grafted somehow "knows" where it is destined to be on the motherboard. This invention relates to a new integration technique based on programmable self-assembly principles encountered in biological systems. This new technique removes the requirement of dimension conservation during the grafting process. Our objective is to demonstrate the self-assembly of micro/nano structures on silicon using DNA (Deoxyribonucleic Acid) polymers as "selective glues", thereby developing techniques for integrating these structures sparsely onto large area motherboards. This brings together with high precision, at low cost, devices made of different materials with different real densities as shown in FIG. 10. This approach relies on the principles of programmable self-assembly found in all biological systems, and uses existing well-understood synthetic DNA chemistry as the enabling process. These techniques include: 1) remove the specialty devices from their mother substrates using the epitaxial lift-off process, 2) attach selective DNA polymer sequences onto the specialty devices using DNA attachment chemistry specially developed in our company, 3) selectively attach complementary DNA polymer sequences to proper locations on the motherboard substrate, and 4) carry out self-assembly by using hybridization of the complementary DNA strands. This uses DNA polymer sequences as a smart and very selective glue to attach micron/nanosize specialty devices to designated areas on a motherboard (see FIG. 11).

Selective DNA Hybridization and Electric Field Transport Techniques

Figure 12:
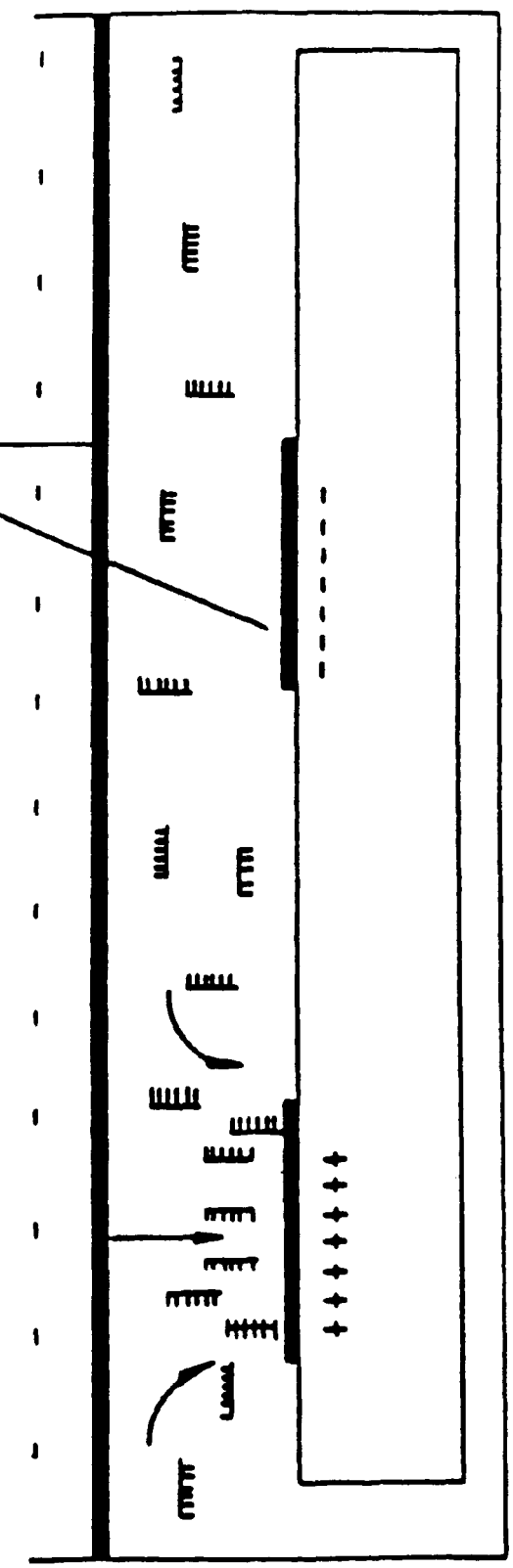
FIG. 12 shows a cross-sectional view of selective electric field deposition of DNA onto the specially derivitized microelectrode surfaces.

Techniques for the hybridization of DNA sequences to complementary DNA sequences attached to solid support materials are well known and used in many biotechnological, molecular biology, and clinical diagnostic applications. In general hybridization reaction are carried out in aqueous solutions which contain appropriate buffer electrolyte salts (e.g., sodium chloride, sodium phosphate). Temperature is an important parameter for controlling the stringency (specificity) and the rate of the hybridization reactions. Techniques exist for hybridization of DNA sequences to semiconductor materials. The first is a UV lithographic method which allow imprinting or patterning of DNA hybridization onto solid supports materials such as silicon dioxide and various metals. The second is a method for electrophoretically transporting DNA-nanostructures (nanostructures to which specific DNA sequences are attached) to selected locations on substrate materials. The technique for UV lithography with DNA involves first coating a substrate material with a molecular layer of specific attachment DNA polymer sequences. An appropriate mask can be used to imprint a pattern into the attachment layer of DNA by exposure to UV irradiation (300 nm) for several seconds. The DNA in the area on the substrate exposed to UV light becomes in-active to hybridization with its complementary DNA sequence i.e., it is not able to form the double-stranded structure. FIG. 7 show fluorescent DNA on a silicon structure was patterned with 10 micron lines using an electron microscope grid pattern. After UV patterning the material is hybridized with a complementary fluorescent labeled DNA probe, and examined epifluorescent microscopy. The fluorescent image analysis shows where the complementary probe has hybridized (fluorescent), and where no hybridization has occurred (no fluorescence). In addition to DNA based UV photolithographic type processes, other electric field based process allows derivitized DNA and charged fluorescent nanospheres to be electrophoretically transported and deposited onto selective microscopic locations on solid supports. The basic method and apparatus for this technology is shown in FIG. 12. Negatively charged DNA, sub-micron or micronscale structures can be suspended in aqueous solutions and transported via an electric field (electrophoresis in solutions) to microscopic locations which are biased positive, relative to other locations which are biased negative. This is a particularly important technique in that it provides a mechanism to direct the transport of specifically labeled devices to specific locations on a substrate material.

Micron/Nanoscale Structure Preparation

The first step in our self-assembly technique is the preparation of the specialty devices to grafting. In this case, the specialty devices are fabricated in a standard fashion on their mother substrates on a sacrificial layer as required by the ELO process. A suitable coating layer is then deposited on these devices to assure they have a Brownian like motion in the saline solution. By controlling the characteristics of the deposited material with respect to device materials the behavior of the devices once released into the saline solution can be controlled. For example, by controlling the coating material properties we could control the direction of the devices in the solution. Once the devices are coated, a thick polyamide film may be spun to provide a physical support to the devices after the ELO process. The ELO process may be carried out and the thin film devices may be separated from their mother substrates. By using plasma etching the polyamide film may be recessed to provide sufficient steps to prevent the metal layer from being continuous. The DNA attachment process is then carried out and a specific DNA sequence may be covalently attach on all the metal surfaces. By irritating with a UV light from the front surface of the devices, the DNA areas that are exposed and not protected, may be destroyed or put in a form that is not suitable for further hybridization. By using a proper solvent the polyamide will then be removed and the devices may be released into the saline solution used for the further hybridization processes.

Preparation of the Motherboard Substrate

To delineate the areas where the grafting of the specialty devices will take place, a selective attachment procedure for the complementary DNA polymer must be carried out. The selective attachment can be realized by using the inherent selectivity of DNA sequences, selective attachment chemistries, or by directed electrophoretic transport. Alternatively after attachment, the DNA strands in unwanted regions can be destroyed by UV radiation. This approach is useful only when one group of devices need to be self-assembled.

As described in earlier sections, DNA attachment chemistry is strongly dependent on the materials used to which the DNA polymers may be attached. For example, to attach DNA to aluminum pads on a silicon chip coated with a protective glass layer, we first activate the aluminum regions by dipping the sample for a short period of time into a dilute buffered HF solution. The end result of this process is that only a few DNA strands are attached to the protective glass layer while the exposed aluminum pads are highly reactive to DNA. This material selectivity is a convenient and general way to attach DNA to the desired regions. When material selectivity is combined with UV directed inactivation and electrophoretic transport process, this allows for repeatable attachment processes to be carried out sequentially. Consider the simultaneous self-assembly of several types of specialty devices. The pads need then to be grouped according to the device to which they are to be coupled. In this case, each pad group needs to be coated with a specific DNA sequence complementary to the DNA sequence attached to the specialty device that it would be bonded to. In order to "pre-program" the motherboard pads, each DNA sequence can be attached sequentially to the proper pads. This can be easily achieved by using the electrophoresis process and by applying a negative potential to the pads where DNA attachment is not desired. Simultaneously, a positive voltage can be applied to enhance attachment to the desired locations. For a second set of DNA sequence attachment, the procedure may be repeated with a different set of programming voltages. Thus, when the self-assembly of multiple device types need to be carried out simultaneously, the motherboard receiving pads may be programmed by applying a proper set of positive and negative potentials to the pads. When only one type of device needs to be self-assembled on the motherboard, the use of the material selectivity of the DNA attachment chemistry alone is sufficient.

Specific DNA Polymers: A Selective Glue

Figure 13:
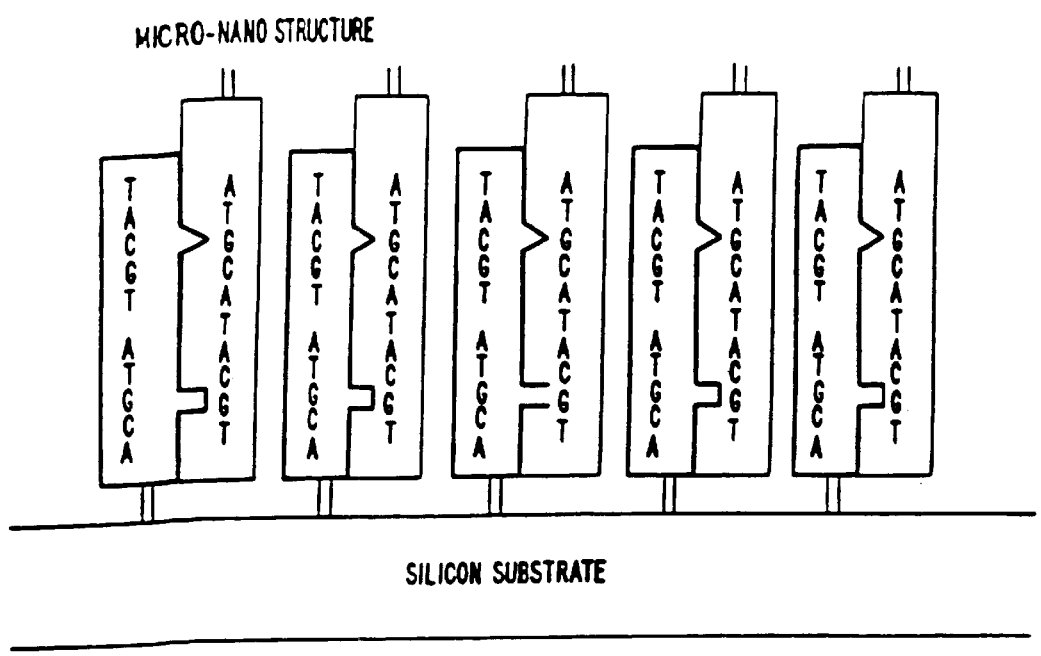
FIG. 13 shows a cross-sectional view of a micro or nanoscale structure coupled to its host mother board substrate by selective DNA hybridization between complimentary DNA strands.

Once the motherboard is pre-programmed and the specialty devices are released and are freely moving in the saline solution bath, the self-assembly process can take place. At the proper (hybridization) stringency temperature, and by agitating gently the devices in the solution, hybridization of complementary DNA strands may be allowed to take place as the proper device-pad pairs come into contact (see FIG. 13). To achieve this process several different methods may be investigated.

Conventional and Electronic Hybridization

In this methods all devices may be released simultaneously into the solution, and the probability of a hybridization process taking place may be related directly to the probability of the proper device-pad pairs to come into contact. Under very simplifying assumptions, the probability of a hybridization $P_h$ may be roughly related to the ratio of the total available pad area $A_p$ to the mother board area $A_{mb}$ $$P_h \, \alpha \, NA_p/A_{mb}$$

where N is the real density of one of the specialty device groups in the solution. Since the probability distribution is expected to be random, this process may take very long times to achieve reasonable hybridization yields. Alternatively it may require the solution to be saturated with the specialty devices. This may increase the cost of the process and limit the number of types of specialty devices that can be self-assembled. In order to improve the selectivity and alignment accuracy several heating and cooling cycles will be carried out during the hybridization process. During the heat cycle, weakly hybridized components may be dissociated away to increase the chance of forming stronger bonds.

Epitaxial Lift-Off Process

A key part of the self-assembly process is the preparation of the micro/nano scale devices for DNA attachment, their handling during the attachment and finally their release into the saline solution prior to hybridization. The most popular ELO approach is to employ the selectivity of dilute HF acid on the Al GaAs series of alloys. The Aluminum rich alloys etch at a rate of approximately 1 mm/hr, while the etch rate of Gallium rich alloys is almost undetectable, less than 0.1 nm/hr. An intermediate layer of AlAs dissolves, allowing upper epitaxial layers to simply float away from the substrate. Other separation methods have also been used, including mechanical cleavage (CLEFT), and total substrate etching down to an etch stop layer. Epitaxial films in the thickness range between 20 nm and 10 mm have been separated from their growth substrates, handled and manipulated.

For example, using this technique thin III-V semiconductor films have been direct-bonded to foreign substrates, such as processed silicon wafers. The mechanical flexibility of ELO films allows a perfect conformation of the films to the substrate topography, which creates a strong and complete bond. The ELO technique then, produces a monolithic-like epitaxial thin film on an engineered substrate. Prior to lift-off, various devices can be fabricated on the films while still on their mother substrates. The ELO technique stands somewhere intermediate between a hybrid approach, such as flip-chip solder bump mounting, and a fully monolithic approach, such as direct hetero-epitaxy; it combines, however, the advantages of both. ELO is a true thin-film technology, allowing thin-film metal wiring which passes back and forth over the edge of a thin III-V film and onto a silicon micro-chip substrate. At the same time, the thin film is grown lattice-matched and essentially homo-epitaxially. Material quality, of the utmost importance for minority carrier devices such as light emitters, is never compromised. Advantages of the ELO technology over hybrid flip-chip: technology include low packaging capacitance and high packing density. For high speed micro-circuits, wiring capacitance must be very low. The penalty is not merely the burden of added power dissipation. Since the series resistance of metal interconnects is not negligible, the RC time constant will ultimately act to limit the speed of opto-electronic micro-circuits irrespective of power dissipation problems, severe as they might be. The ultimate achievable packing density is somewhat scaled with respect to the working dimension of technologies. Therefore, the ELO may offer more in this aspect than the solder bump technique.

ELO films grafting on processed silicon micro-circuits requires consideration of the ultra-fine scale roughness of the deposited oxide surfaces of the micro-chip. Surface roughness interferes with the quality of the Van der Waals or metallurgical bond.

Sequential Hybridization Under DC Electric Field

To increase the probability of hybridization, a second method is to introduce each device group separately and to confine the specialty devices within regions near the positively biased pads. This confinement can be done under the influence of a DC electric field by applying a suitable positive voltage to the pads. The effect of the electric field can then be viewed as increasing the ratio of the areas, or equivalently increasing the device density, N, in the above equation. However, in this case each device group must be introduced sequentially, so the unwanted device groups do not screen the right devices from reaching the pad.

Parallel Hybridization Under an AC Electric Field

The disadvantage of the sequential hybridization is that it increases the cost of manufacturing as the types of specialty devices is increased. An alternative method is to introduce all device types concurrently into the solution, to apply an initial DC voltage to create a distribution of the devices around each pad, and then to apply an AC voltage at a suitable frequency to eliminate the screening effect of the unwanted devices types. The effect of the AC field can be seen as a stronger stirring mechanism.

Metallurgical bonds

Figure 14:
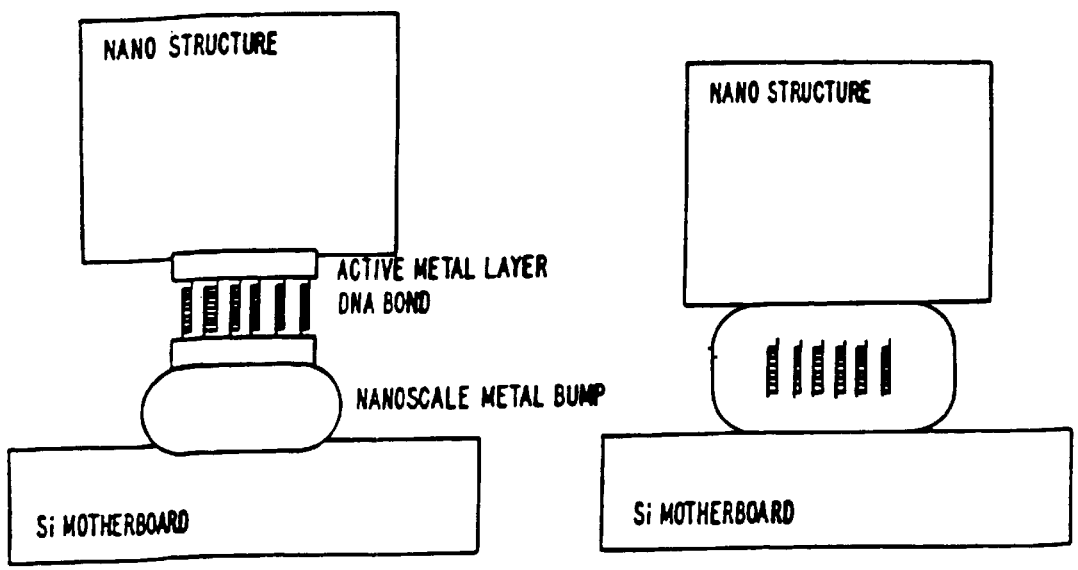
FIG. 14 shows a cross-sectional view of nanostructures held in place via a DNA bond (left-hand side) and nanostructure held by a metallurgical contact after a high temperature cycle (right-hand side).

After the hybridization process the specialty devices are held in their proper places through the formation of the double-stranded DNA structure which has very high bonding strength. The entire assembly is then cleaned by rinsing and then dried. At this point there is no electrical contact between the motherboard and the specialty devices. The DNA bond strength remains in the solid state and serves to keep the devices in place. One method to achieve a metallurgical bond with ohmic contact is to use conductive materials on the pads and devices that can be bonded together eutectically at low temperatures. A second method is to use metals with low melting temperatures like solder or indium under a metal layer that is active for DNA attachment. In this case the bumps must be made in nanometer dimensions. While the device are held in place by the DNA bonds, in both cases the application of heat will result in the formation of a metallurgical bond and an ohmic contact. The DNA polymer will remain within the bond but may only contribute to an increased contact resistance depending on the initial DNA loading factor used. FIG. 14 shows a the process described above.

Alignment and Orientation of the Specialty Devices

One of the critical issues that needs to be addressed in the self-assembly approach is the accuracy with which the specialty devices can be aligned to the pads on the motherboard. We will first assume that the specialty devices have a circular base such that the process is rotation invariant. In this case, it is expected that if the pad diameter is d, an alignment accuracy of d/2 could be achieved with the DNA bonding process. Devices that are misaligned with more than d/2 misalignment will not form a strong bond during the hybridization process and would not be held in place during the heating and cooling cycles of the hybridization process. In addition, if the nano-bump technology outlined in the previous section is employed, after the high temperature cycle for forming the metallurgical bonds, the devices may be self-aligned to the pads in a similar fashion as with the C4 technology used for flip-chip bonding.

Figure 15:
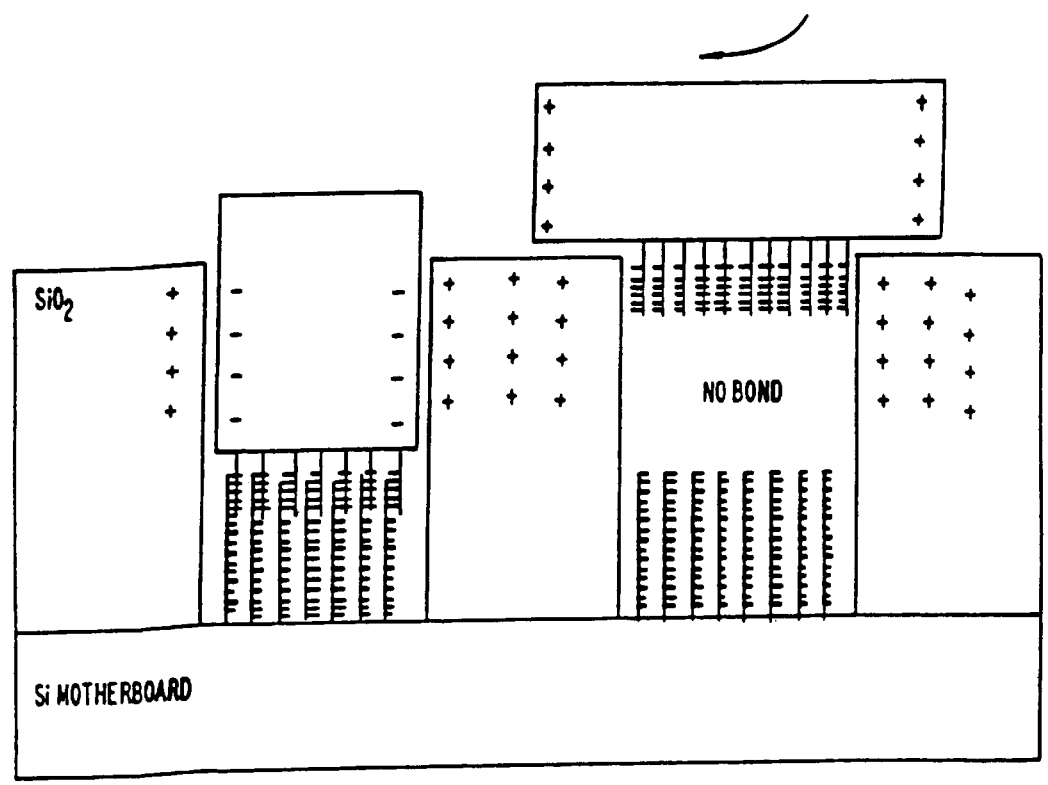
FIG. 15 shows a cross-sectional view of an apparatus for the orientation of specialty devices prior to hybridization by physical masking and charge guiding.
Figure 16:
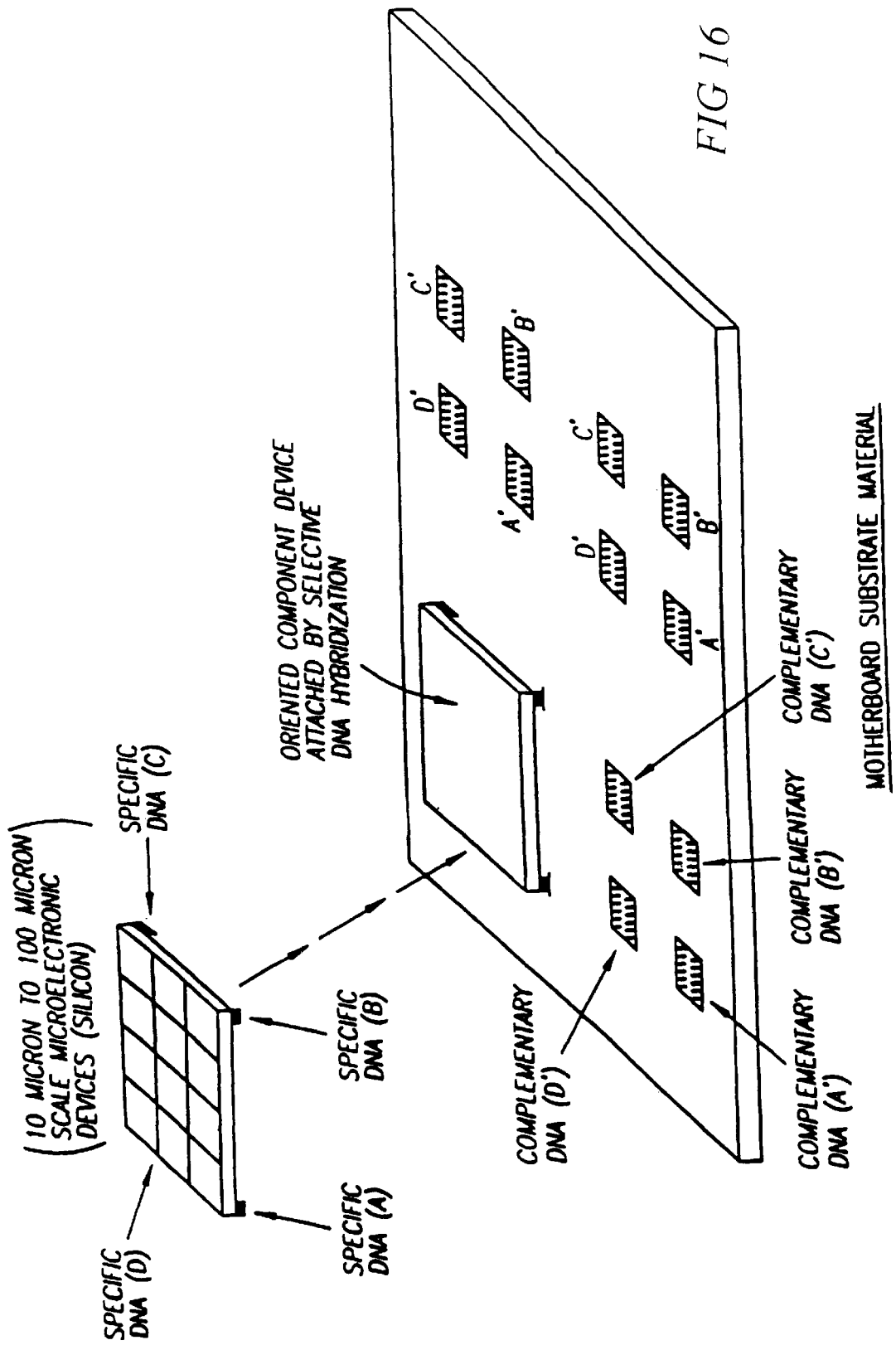
FIG. 16 shows an apparatus for attachment and orientation of larger sized devices onto a substrate or motherboard.
Figure 17:
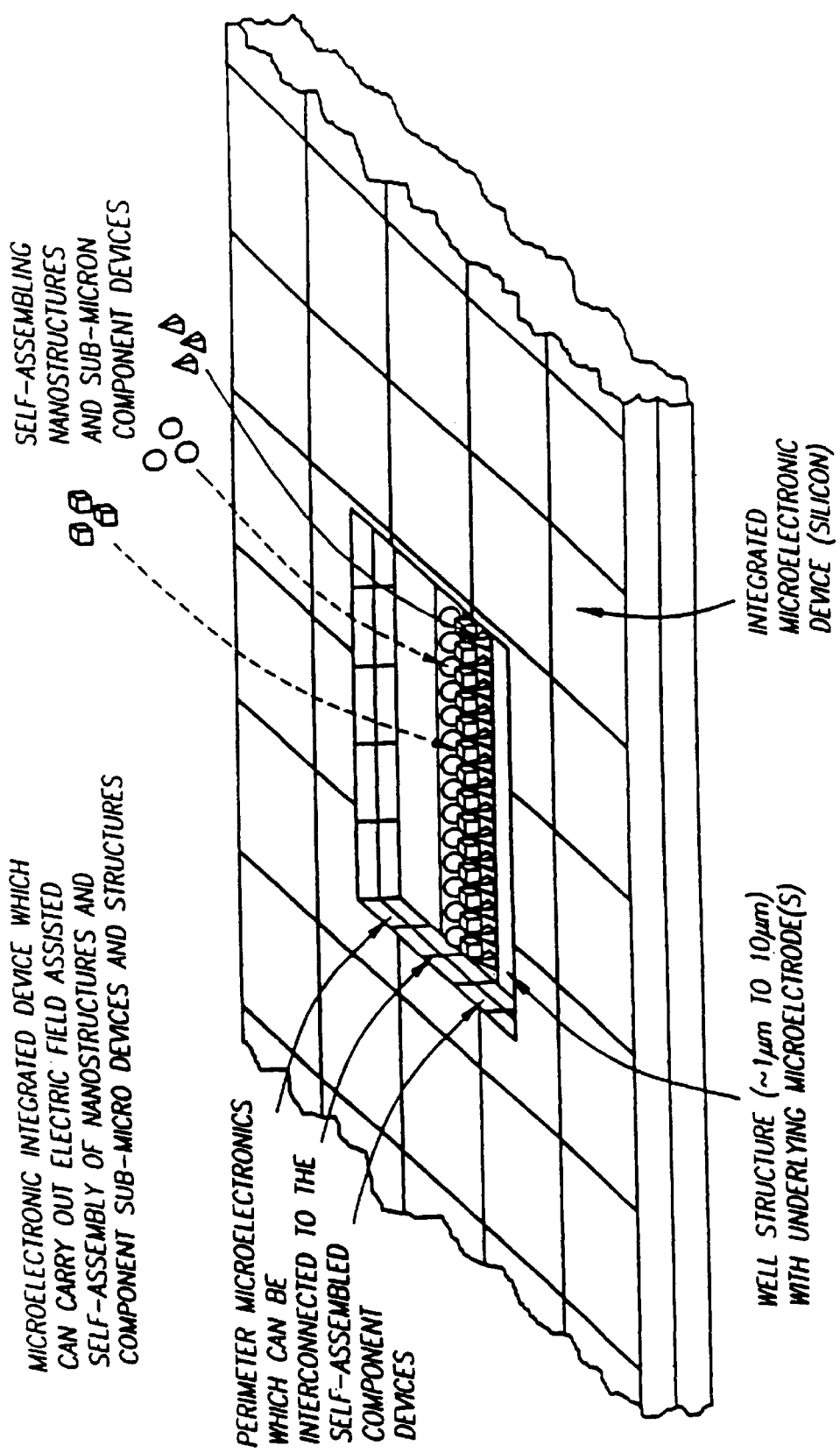
FIG. 17 shows an apparatus for fabrication of nanostructures.

A more difficult issue arises if the specialty device do not have a circular symmetric base and need to be placed with a certain orientation on the pads. Two different approaches for bonding with the proper orientation may be used. As a first approach, properly patterned silicon dioxide layers are used to physically mask out specialty devices with the wrong orientations as shown in FIG. 15. The devices will fit onto the pads only if they possess the right orientation. Another approach to orient the device is to use coulombic forces prior to the hybridization of DNA. By ion implantation, or e-beam lithography exposure an opposite sign charge build-up can be realized in certain locations on the pads and on the devices. These charge patterns guide the devices to their proper orientations. As can be seen in FIG.

15, both approaches can be used together to provide DNA bonding with proper orientation of the specialty devices.

Although the foregoing invention has been described in some detail by way of illustration and example for purposes of clarity and understanding, it may be readily apparent to those of ordinary skill in the art in light of the teachings of this invention that certain changes and modifications may be made thereto without departing from the spirit or scope of the appended claims.

We claim:

1. A method for the electroosmotic movement and attachment of microscale and nanoscale component devices comprising the step of:

providing a planar transport surface for supporting the electroosmotic transport of the component device, wherein the planar transport surface has at least one target electrode, the target electrode having an upper surface co-planar with the planar transport surface;

providing a drive electrode on the planar transport surface, the drive electrode being coplanar with and above the transport surface;

providing a first component device and a fluidic medium in contact with the planar transport surface, target electrode, and drive electrode;

activating the drive electrode to effect electroosmotic transport of the component device across the transport surface to the target electrode; and attaching the component device to the planar transport surface.

2. The method of claim 1 wherein the electroosmotic force is created at least in part by the target electrode.

3. The method of claim 1 wherein the electrode is provided proximal to the target electrode.

4. The method of claim 1 further including the step of electrically activating the component device attached to the transport surface.

5. The method of claim 1 wherein the component device is a microelectronic component device.

6. The method of claim 5 wherein the microelectronic component device is a light emitting diode (LED).

7. The method of claim 1 wherein the component device is a micromechanical device.

8. The method of claim 1 wherein the activating step includes an electrophoretic force in addition to the electroosmotic force.

9. The method of claim 1 wherein the activating step includes an electrostatic force in addition to the electroosmotic force.

10. The method of claim 1 wherein the activating step includes a dielectrophoretic force in addition to the electroosmotic force.

11. The method of claim 1 wherein the activating step involves serial steps of placement of a single component device.

12. The method of claim 1 wherein multiple component devices are placed in parallel.

* * * * *